(12) United States Patent
Shih et al.

(10) Patent No.: US 12,590,160 B2
(45) Date of Patent: *Mar. 31, 2026

(54) MITIGATION AND REVERSAL OF INTESTINAL FIBROSIS AND INFLAMMATION BY INHIBITION OF TL1A FUNCTION

(71) Applicant: CEDARS-SINAI MEDICAL CENTER, Los Angeles, CA (US)

(72) Inventors: David Q. Shih, La Crescenta, CA (US); Stephan R. Targan, Santa Monica, CA (US); Dalin Li, Walnut, CA (US); Janine Bilsborough, Adelaide (AU)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 17/814,704

(22) Filed: Jul. 25, 2022

(65) Prior Publication Data

US 2023/0091596 A1 Mar. 23, 2023

Related U.S. Application Data

(63) Continuation of application No. 16/798,030, filed on Feb. 21, 2020, now Pat. No. 11,434,296, which is a
(Continued)

(51) Int. Cl.
*A61K 39/395* (2006.01)
*C07K 16/24* (2006.01)
(Continued)

(52) U.S. Cl.
CPC ...... *C07K 16/2866* (2013.01); *A61K 39/3955* (2013.01); *C07K 16/241* (2013.01);
(Continued)

(58) Field of Classification Search
None
See application file for complete search history.

(56) References Cited

U.S. PATENT DOCUMENTS 7,708,996 B2 5/2010 Yu et al.
8,017,122 B2 9/2011 Siadak et al.
(Continued)

FOREIGN PATENT DOCUMENTS

CN 101198624 A 6/2008
CN 101903402 A 12/2010
(Continued)

OTHER PUBLICATIONS

Shih et al., Reversal of Murine Colitis and Fibrosis by Neutralizing TL1A Antibody: Potential Novel Therapy to Alter Natural History of Crohn's Disease, Gastroenterology, vol. 142, Issue 5, Supplement 1, p. S-84, Abstract 357, May 2012.*
(Continued)

*Primary Examiner* — Claire Kaufman
(74) *Attorney, Agent, or Firm* — JONES DAY

(57) ABSTRACT

The invention relates to methods of treating fibrosis and inflammatory bowel disease. In one embodiment, the present invention treats gut inflammation by administering a therapeutically effective dosage of TL1A inhibitors and/or DR3 inhibitors to an individual. In another embodiment, the present invention provides a method of reversing tissue fibrosis in an individual by inhibiting TL1A-DR3 signaling function.

9 Claims, 35 Drawing Sheets
(21 of 35 Drawing Sheet(s) Filed in Color)

Related U.S. Application Data continuation of application No. 14/779,893, filed as application No. PCT/US2014/032054 on Mar. 27, 2014, now Pat. No. 10,633,449.

(60) Provisional application No. 61/872,020, filed on Aug. 30, 2013.

(51) Int. Cl.

| | |
|---|---|
| *C07K 16/28* | (2006.01) |
| *C12N 15/113* | (2010.01) |
| *C12Q 1/68* | (2018.01) |
| *G01N 33/68* | (2006.01) |
| *C12Q 1/6883* | (2018.01) |

(52) U.S. Cl.
CPC ...... *C07K 16/2875* (2013.01); *C07K 16/2878* (2013.01); *C12N 15/1138* (2013.01); *G01N 33/6869* (2013.01); *C07K 16/24* (2013.01); *C07K 2317/76* (2013.01); *C12Q 1/6883* (2013.01); *C12Q 2600/112* (2013.01); *C12Q 2600/158* (2013.01); *G01N 2333/7155* (2013.01); *G01N 2800/065* (2013.01); *G01N 2800/10* (2013.01)

(56) References Cited

U.S. PATENT DOCUMENTS

| | | | |
|---|---|---|---|
| 8,263,743 | B2 | 9/2012 | Smith et al. |
| 9,068,003 | B2 | 6/2015 | Siegel et al. |
| 9,682,923 | B2 * | 6/2017 | Baroni ..................... A61P 1/04 |
| 10,633,449 | B2 | 4/2020 | Shih et al. |
| 11,136,386 | B2 | 10/2021 | Kruidenier et al. |
| 11,434,296 | B2 | 9/2022 | Shih et al. |
| 2007/0160611 | A1 | 7/2007 | Yao et al. |
| 2009/0220417 | A1 | 9/2009 | Siadak et al. |
| 2009/0317388 | A1 | 12/2009 | Burkly et al. |
| 2010/0190162 | A1 | 7/2010 | Rotter et al. |
| 2011/0003707 | A1 | 1/2011 | Goix et al. |
| 2012/0079611 | A1 | 3/2012 | Shih et al. |
| 2012/0263718 | A1 | 10/2012 | Siegel et al. |
| 2012/0315282 | A1 | 12/2012 | Bedinger et al. |
| 2013/0137680 | A1 | 5/2013 | Boyer et al. |
| 2014/0255302 | A1 | 9/2014 | Poulton et al. |
| 2016/0096885 | A1 | 4/2016 | Shih et al. |
| 2023/0272098 | A1 | 8/2023 | Kruidenier et al. |
| 2023/0304095 | A1 | 9/2023 | McGovern et al. |
| 2024/0309104 | A1 | 9/2024 | Luo et al. |

FOREIGN PATENT DOCUMENTS

| | | | |
|---|---|---|---|
| JP | 2009526756 | A | 7/2009 |
| WO | WO-2006122079 | A1 | 11/2006 |
| WO | WO-2007133816 | A2 | 11/2007 |
| WO | WO-2009064854 | A2 | 5/2009 |
| WO | WO-2014160883 | A1 | 10/2014 |
| WO | WO-2014186665 | A2 | 11/2014 |

OTHER PUBLICATIONS

Kidd et al., CTGF, intestinal stellate cells and carcinoid fibrogenesis, World J. Gastroenterol. 13(39):5208-5216, Oct. 21, 2007.*
Guo-Qiu et al., The Level of Connective Tissue Growth Factor in Sera of Patients with Hepatitis B Virus Strongly Correlates with Stage of Hepatic Fibrosis, Viral Immunol. 23(1):71-78, 2010.*
Vozenin-Brotons et al., Fibrogenic signals in patients with radiation enteritis are associated with increased connective tissue growth factor expression, Int. J. Rad. Oncol. 56(20):561-572, Jun. 1, 2003.*
Dendooven et al., Connective tissue growth factor (CTGF/CCN2) Elisa: a novel tool for monitoring fibrosis, Biomarkers, 16(4):289-301, May 2011.*

Leask et al., Connective tissue growth factor (CTGF, CCN2) gene regulation: a potent clinical bio-marker of fibroproliferative disease?, J. Cell. Commun. Signal. 3:89-94, 2009.*
Di Mola et al., Differential Expression of Connective Tissue Growth Factor in Inflammatory Bowel Disease, Digestion, 69:245-253, 2004.*
Selet Science, FlowCytomix Announces New Multiplexing Kits for Assessing T Helper Cell Differentiation, Retrieved online from: <URL:https://www.selectscience.net/article/flowcytomix-announces-new-multiplexing-kits-for-assessing-t-helper-cell-differentiation> [retrieved on Apr. 30, 2025], 2025.*
Mifflin et al., Intestinal myofibroblasts: targets for stem cell therapy, J. Physiol. Gastrointest. Liver Physiol. 300(5):G684-G696, 2011.*
Welz et al., Fibrosis and Inflammation in Inflammatory Bowel Disease—More Than 2 Sides of the Same Coin?, Gatroenterol. 164(1):19-21, Jan. 2023.*
Adler et al.: Anti-tumor necrosis factor [alpha] prevents bowel fibrosis assessed by messenger RNA, histology, and magnetization transfer MRI in rats with Crohn's disease. Inflamm Bowel Dis 19(4):683-690 (2013).
Andoh et al.: Mucosal cytokine network in inflammatory bowel disease. World J Gastroenterol. 14(33):5154-5161 (2008).
Bamias et al.: Expression, localization, and functional activity of TL1A, a novel Th1-polarizing cytokine in inflammatory bowel disease. Journal of Immunology 171(9):4868-4874 (2003).
Bamias et al.: Role of TL1A and its Receptor DR3 in Two Models of Chronic Murine Ileitis, PNAS, 103(22):8441-8446, 2006.
Barrett et al.: Constitutive TL1A Expression under Colitogenic Condition Modulates the Severity and Location of Gut Mucosal Inflammation and Induces Fibrostenosis, American Journal of Pathology, 180(2):636-649 (2012).
Bioque et al.: Further evidence for a genetic association of interleukin-1 receptor antagonist and ulcerative colitis in the Northern and Mediterranean population. Gastroenterology 108:a783 (1995) Abstract only.
Brand et al.: IL-22 is increased in active Crohn's disease and promotes proinflammatory gene expression and intestinal epithelial cell migration. Am J Physiol Gastrointest Liver Physiol. 290:G827-838 (2006).
Bull et al.: The death receptor 3-TNF-like protein 1A pathway drives adverse bone pathology in inflammatory arthritis. J.Exp. Med., 205(11):2457-2464, 2008.
Burke et al.: Transcriptomic analysis of intestinal fibrosis-associated gene expression in response to medical therapy in Crohn's disease. Inflammatory Bowel Diseases. 14(9):1197-1204 (2008).
Camoglio et al.: Altered expression of interfero-gamma and interleukin-4 in inflammatory bowel disease; Inflamm Bowel Dis., 4(4): 285-290; Abstract only (1998).
Chen et al.: Discordant protein and mRNA expression in lung adenocarcinomas. Mol. Cell. Proteomics, 4:304-313, 2002.
Chen et al.: Screening for genes associated with cardiac fibrosis induced by aldosterone. Xi Bao Yu Fen Zi Mian Yi Xue Za Zhi Journal of Cellular and Molecular Immuno 28(4):350-353 (2012) (English Abstract & Translation).
Dambacher et al.: Interleukin 31 mediates MAP kinase and STAT⅓ activation in intestinal epithelial cells and its expression is upregulated in inflammatory bowel disease. Gut. 56:1257-1265 (2007).
Duerr et al.: Association between ulcerative colitis and a polymorphism in intron 2 of the interleukin-2 receptor antagonist gene. Gastroenterology Abstract Only 108:a812 (1995).
European Patent Application No. EP14773989.0 Strawman Limited Opposition Against EP2978440 dated Jul. 1, 2020.
Fessler et al.: A genomic and proteomic analysis of activation of the human neutrophil by Lipopolysaccharide and its mediation by p38 mitogen-activated protein kinase. The Journal of Biological Chemistry, 277(35):31291-31302, 2002.
Fitzpatrick, LR, Novel Pharmacological Approaches for Inflammatory Bowel Disease: Targeting Key Intracellular Pathways and the IL-23/IL-17 Axis, International Journal of Inflammation, vol. 2012, pp. 1-8.
Gologan et al.: Inflammatory gene expression profiles in Crohn's disease and ulcerative colitis: A comparative analysis using a

(56)            References Cited

OTHER PUBLICATIONS reverse transcriptase multiplex ligation-dependent probe amplification protocol. Journal of Crohn's and Colitis. 7:622-630 (2013).

Halme et al.: Family and twin studies in inflammatory bowel disease. World J Gastroenterol. 12(23):3668-3672 (2006).

Hsu et al.: The tale of TL1A in inflammation. Mucosal Immunol 4(4):368-370, 2011.

Koga et al.: Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.

Mansfield et al.: Novel genetic association between ulcerative colitis and the antiinflammatory cytokine interleukin-1 receptor antagonist. Gastroenterology 106:637-642 (1994).

Mazzei et al.: Suppression of intestinal inflammation and inflammation-driven colon cancer in mice by dietary sphingomyelin: importance of PPAR-γ expression. J Nutr Biochem. 22(12):1160-1171 (2011) doi:10.1016/j.jnutbio.2010.09.017.

Meylan et al.: The TNF-family cytokine TL1A drives IL-13 dependent small intestinal inflammation. Muscosal Immunol., 4(2):172-185, 2011.

Migone et al.: TL1A is a TNF-like Ligand for DR3 and TR6/DcR3 and Functions as a T cell Costimulator, Immunity, 16:479-492, 2002.

Muzes et al.: Changes of the cytokine profile in inflammatory bowel diseases. World J Gastroenterol. 18(41):5848-5861 (2012).

NCBI Gene Database. Gene ID: 133396, IL31RA interleukin 31 receptor A [Homo sapiens (human)], [Retrieved online Aug. 31, 2018] Retrieved from https://www.ncbi.nlnnih.gov/gene/133396#gene-expression., Aug. 5, 2018 (16 pgs).

NCBI Gene Database, Gene ID: 3458, IFNG interferon gamma [Homo sapiens (human)], [Retrieved online Aug. 31, 2018] Retrieved from <url:<a href="https://www.ncbi.nlnnih.gov/gene/3458#gene-expression>">https://www.ncbi.nlnnih.gov/gene/3458#gene-expression., Aug. 25, 2018 (16 pgs).</url:<a>.

Ostanin et al.: T cell transfer model of chronic colitis: consents, considerations, and tricks of the trade. Am J Physiol Gastrointest Liver Physiol. 296(2):G135-G146 (2009).

Papadakis et al.: Dominant Role for TL1A/DR3 Pathway in IL-12 plus IL-18-Induced IFN-γ Production by Peripheral Blood and Mucosal CCR9+ T Lymphocytes. the Journal of Immunology. 174:4985-4900 (2005).

Papadakis et al.: IL1A synergizes with IL-12 and IL-18 to enhance IFN-y production in human T cells and NK cells, The Journal of Immunology, 172:7002-7007, 2004.

Parente et al.: Bowel Ultrasound in Assessment of Crohn's Disease and Detection of Related Small Bowel Strictures: A Prospective Comparative Study Versus X Ray and Intraoperative Findings, Gut, 50: 490-495, 2002.

PCT/US2014/032054 International Search Report and Written Opinion dated Aug. 5, 2014, 14 pages.

Pinchuk et al.: Human Colonic Myofibroblast Promote Expansion of CD4+ CD25high Foxp3+ Regulatory T Cells, Gastroenterology, 140(7):2019-2030, pp. 1-19, and p. 8, 2011.

Prometheus Biosciences, Inc. Form S-1 Registration Statement as filed with the Securities and Exchange Commission on Feb. 19, 2021 (246 pages).

Rieder et al.: Intestinal Fibrosis in Inflammatory Bowel Disease—Current Knowledge and Future Perspectives, J.Crohns Colitis, 2:279-290, 2008.

Rieder et al.: Managing Intestinal Fibrosis in Patients With Inflammatory Bowel Disease. Gastroenterol Hepatol (NY). 14(2):120-122 (2018).

Shih et al.: Constitutive TL1A (TNFSF15) Expression on Lymphoid or Myeloid Cells Leads to Mild Intestinal Inflammation and Fibrosis, PLOS One, 6(1), pp. 1-16, 2011.

Shih et al.: Inhibition of a novel fibrogenic factor TI 1a reverses established colonic fibrosis. Mucosal Immunol., 7(6):1492-1503, 2014.

Spinelli et al.: Intestinal Fibrosis in Crohn's Disease: Medical Treatment or Surgery?, Current Drug Targets, 11(2):242-248, 2010.

Strober et at, Proinflammatoly Cytokines in Pathogenesis of Inflammatory Bowel Diseases, Gastroenterology, 140(6):1756-1767, 2011.

Takedatsu et al.: TL1A (TNFSF15) Regulates the Development of Chronic Colitis by Modulating both T helper (TH) 1 and TH17 Activation; Gastroenterology; HHS Public Access; 135(2): 552-567 (2008).

Tountas et al.: Genetic association between allele 2 of IL-1 receptor antagonist (IL-1 ra) and ulcerative colitis in Los Angeles based hispanic population. Abstract XP000673112 only. Gastroenterology 108:806-813 (1995).

Tountas et al.: Heterogenous association between allele 2 of IL-2 receptor antagonist (ILC4371 RA) and ulcerative colitis in Jewish and non-Jewish populations. Abstract XP000673114 only. J. Investigative Medicine 44(1) (1996).

UniprotKB Database, Q8NI17 (IL31R_Human), Retrieved online Sep. 5, 2019. Retrieved from <url <a= href=>https://www.uniprot.org/uniprot/Q8NI17. Jul. 31, 2019.</url>.

U.S. Appl. No. 14/779,893 Final Office Action dated Apr. 26, 2019.

U.S. Appl. No. 14/779,893 Office Action dated Jul. 5, 2017.

U.S. Appl. No. 14/779,893 Office Action dated Mar. 21, 2018.

U.S. Appl. No. 14/779,893 Office Action dated Sep. 12, 2019.

U.S. Appl. No. 14/779,893 Office Action dated Sep. 7, 2018.

U.S. Appl. No. 16/388,101 Restriction Requirement dated Jul. 10, 2020.

U.S. Appl. No. 16/798,030 Office Action dated Oct. 29, 2021.

Yagi et al.: Interleukin-31 stimulates production of inflammatory mediators from human colonic subepithelial myofibroblasts. International Journal of Molecular Medicine, 19:941-946, 2007.

Zhang et al.: Structures and biological functions of IL-31 and IL-31 receptors. Cytokine Growth Factor. 19(5-6):347-356 (2008).

Zheng et al.: 2013 AGA Abstracts 2013 Gastroenterol. 144(5): Supplement 1: p. S-132; Abstract 735 (2013).

Zheng et al.: Dynamic expression and significance of IL-31 in the process of pulmonary fibrosis in experimental mice. Shadong Medical Journal. 49(13):26-27 (2009).

Zheng et al.: Sustained TL1A (TNFSF15) Expression on both Lymphoid and Myeloid Cells Leads to Mild Spontaneous Intestinal Inflammation and Fibrosis. European Journal of Microbiology and Immunology 3(1):11-20 (2013).

Cornelissen, Christian. et al. Signaling by IL-31 and functional consequences. European journal of cell biology 91(6-7):552-566 (2012).

EP20190199149.6 Notice of Opposition, Office Action dated Jun. 7, 2024.

Flier, Sarah N. et al. Identification of epithelial to mesenchymal transition as a novel source of fibroblasts in intestinal fibrosis. The Journal of biological chemistry 285(26):20202-20212 (2010).

Gonsky, R. et al. DOP29 Elevation of a novel blood-based gene signature in a severe Crohn's disease (CD) subtype preceding surgery defines and predicts a post-surgical decrease in pro-inflammatory pathway activation. Journal of Crohn's and Colitis 14(Supplement_1): S068-S069 (2020).

Speca, Silvia. et al. Cellular and molecular mechanisms of intestinal fibrosis. World journal of gastroenterology 18(28):3635-3661 (2012).

Zhang, Xiaolan. et al. Tu1650 Constitutive TL1A Expression Modulates Colonic Fibrosis on TNBS-Induced Colitis in Mice. Gastroenterology 144(5):S-814 (2013).

Zheng, Libo. et al. Sustained TL1A (TNFSF15) Expression on both Lymphoid and Myeloid Cells Leads to Mild Spontaneous Intestinal Inflammation and Fibrosis (along with Evidence of publication date). European Journal of Microbiology and Immunology 3(1):11-20 (2013).

Anonymous: EP4285988 Third Party Observation dated Nov. 20, 2024 (6 pages).

Arai et al.: Interleukin-31 Receptor A Expression in the Dorsal Root Ganglion of Mice with Atopic Dermatitis. International Journal of Molecular Sciences. 24:1047 pp. 1-16 (2023).

Co-pending U.S. Appl. No. 18/557,551, inventors Potdar; Alka et al., filed Oct. 26, 2023.

Co-pending U.S. Appl. No. 18/645,261, inventors Watkins; Jeffry D. et al., filed Apr. 24, 2024.

(56) References Cited

OTHER PUBLICATIONS

Co-pending U.S. Appl. No. 18/649,944, inventors Stephan; R. Targan et al., filed Apr. 29, 2024.

Mori, Toshifumi. et al. Role and interaction of connective tissue growth factor with transforming growth factor-β in persistent fibrosis: A mouse fibrosis model. Journal of cellular physiology 181(1):153-159 (1999).

Roestenberg, Peggy. et al. Temporal expression profile and distribution pattern indicate a role of connective tissue growth factor (CTGF/CCN-2) in diabetic nephropathy in mice. American Journal of Physiology—Renal Physiology 290(6):F1344-F1354 (2006).

Yokoi, Hideki. et al. Role of connective tissue growth factor in fibronectin expression and tubulointerstitial fibrosis. American Journal of Physiology—Renal Physiology 282(5):F933-F942 (2002).

* cited by examiner

Rag Co          Pre-Tx          Iso Ab

Tl1a-Ab-20mg/kg     Tl1a-Ab-80mg/kg

Blue- DAPI  Green – Vimentin  Red – αSMA  → Activated fibroblast

Dr3 endogenous locus

Dr3 recombined locus

Dr3 Flp-excised locus

Dr3 Cre-excised locus

KO band
506 bp

WT band
353 bp

Colon

MITIGATION AND REVERSAL OF INTESTINAL FIBROSIS AND INFLAMMATION BY INHIBITION OF TL1A FUNCTION

CROSS-REFERENCE TO RELATED APPLICATIONS

This application is a continuation of U.S. application Ser. No. 16/798,030, filed Feb. 21, 2020, now issued as U.S. Pat. No. 11,434,296 on Sep. 6, 2022, which is a continuation of U.S. application Ser. No. 14/779,893 filed Sep. 24, 2015, now issued as U.S. Pat. No. 10,633,449 on Apr. 28, 2020, which is a National Phase of International Application No. PCT/US2014/032054 filed Mar. 27, 2014, which claims the benefit of U.S. Provisional Application No. 61/872,020 filed Aug. 30, 2013, the entirety of which are hereby incorporated by reference.

FIELD OF INVENTION

The invention provides methods and compositions for the treatment and diagnosis of conditions related to tumor necrosis factor-like cytokine 1A (TL1A) function and fibrosis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) is a chronic inflammatory condition with pathological features such as patchy transmural inflammation and fibrostenosis. Despite potent anti-inflammatory therapies, up to 20% of CD patients still develop stricturing complications that require surgical intervention. Pathways that regulate fibrosis may be distinct from those mediating inflammation. TL1A, a member of the TNF superfamily, binds to death domain receptor 3 (DR3) and modulates the adaptive immune response. TL1A may be associated with CD, intestinal fibrostenosis, and greater need for surgery. There is a need for novel and effective therapeutics for the treatment of diseases associated with the TL1A/DR3 signaling pathway, CD, as well as associated complications including therapeutics for reversal of established fibrosis.

SUMMARY OF THE INVENTION

Various embodiments herein include a method of treating fibrosis in a subject, comprising providing a composition comprising one or more inhibitors of TL1A function, and administering a therapeutically effective dosage of the composition to the subject. In other embodiments, the composition comprises one or more TL1A blocking antibodies. In another embodiment, the composition comprises one or more DR3 blocking antibodies. In another embodiment, the composition comprises one or more compounds that inhibit TL1A function by directly binding to TL1A. In another embodiment, the composition comprises one or more inhibitors of Ifngamma, IL17, Ctgf and IL31Ra. In another embodiment, the composition comprises one or more inhibitors of Tgfbeta1 and Igf1. In another embodiment, the composition comprises one or more inhibitors of IL31 signaling. In another embodiment, administering a therapeutically effective dosage of the composition results in reversal of the fibrosis to pre-inflamed levels. In another embodiment, the fibrosis is colonic fibrosis. In another embodiment, administering a therapeutically effective dosage of the composition further results in inhibition of gut inflammation in the subject.

Other embodiments include a method of treating a disease in a subject, comprising providing a composition comprising an inhibitor of IL31Ra signaling, and administering an effective dosage of the composition to the subject. In another embodiment, the disease is a TL1A associated disease. In another embodiment, the disease is Inflammatory Bowel Disease (IBD). In another embodiment, the disease is associated with strictures developed in the small intestine and/or gut inflammation. In another embodiment, the disease is small and large intestinal fibrostenosis. In another embodiment, the disease is fibrosis. In another embodiment, the composition comprises one or more TL1A antibody. In another embodiment, the composition comprises one or more inhibitors of IL31Ra, IFNgamma, IL17, Ctgf, Tgfβ1 and/or Igf1 signaling.

Other embodiments include a method of diagnosing susceptibility to a TL1A associated disease in a subject, comprising obtaining a sample from the subject, assaying the sample to determine the presence or absence of a high level of IL31Ra expression relative to a normal individual, and diagnosing susceptibility to the TL1A associated disease based on the presence of the high level of IL31 expression relative to a normal individual. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises determining the presence of a high level of expression relative to a normal individual of IL31Ra, IFNgamma, IL17, Ctgf, Tgfβ1 and/or Igf1.

Various embodiments include a method of diagnosing a TL1A associated disease in a subject, comprising obtaining a sample from the subject, assaying the sample to determine the presence or absence of one or more risk variants and/or markers associated with the TL1A associated disease, and diagnosing the TL1A associated disease based on the presence of one or more risk variants and/or markers associated with the TL1A associated disease. In another embodiment, the one or more risk variants and/or markers include a high expression of IL31Ra. Other embodiments include one or more risk variants and/or markers that include a high expression of IFNgamma, IL17, Ctgf, Tgfβ1 and/or Igf1. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises treating the TL1A associated disease by administering one or more TL1A inhibitors. In another embodiment, the method further comprises treating the TL1A associated disease by administering a TL1A inhibitor. In another embodiment, the subject is human. In another embodiment, the method further comprises treating the TL1A associated disease by administering a DR3 inhibitor.

Other embodiments include a method of treating fibrosis in a subject, comprising providing a composition comprising a TL1A inhibitor and DR3 inhibitor, and administering a therapeutically effective dosage of the composition to the subject. In another embodiment, the TL1A inhibitor is a TL1A antibody.

Other embodiments include a method of reversing fibrosis in a subject, comprising providing a composition comprising a TL1A inhibitor and DR3 inhibitor, and administering a therapeutically effective dosage of the composition to the subject. In another embodiment, the composition further comprises an inhibitor of IFNgamma, IL17, Ctgf and/or IL31Ra signaling function.

Various embodiments include a method of treating inflammation, comprising providing a composition comprising a TL1A inhibitor and/or DR3 inhibitor, and administering a therapeutically effective dosage of the composition to the subject. In another embodiment, the composition further comprises an inhibitor of IFNgamma, IL17, Ctgf and/or IL31Ra signaling function.

Other embodiments include a method of treating a disease in a subject, comprising inhibiting Ifnγ and IL-17 expression, down-regulating Tgfβ signaling, and/or reducing fibroblast/myofibroblast, and treating the subject. In another embodiment, the disease is inflammatory bowel disease. In another embodiment, the disease is fibrosis. In another embodiment, the disease gut inflammation. In another embodiment, the disease is complications associated with inflammatory bowel disease.

Other embodiments include a composition comprising one or more inhibitors of TL1A, DR3 and IL31Ra signaling function, and a pharmaceutically acceptable carrier. In another embodiment, the one or more TL1A inhibitors is a TL1A antibody. In another embodiment, the one or more DR3 inhibitors is a DR3 antibody.

Various embodiments herein include a method of treating complications associated with IBD, comprising providing a composition comprising an inhibitor of TL1A, DR3 and IL31Ra signaling function, and administering a therapeutically effective dosage of the composition to the subject. In another embodiment, the composition is administered intravenously to the subject.

BRIEF DESCRIPTION OF THE FIGURES

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

FIG. 1A depicts TL1A Ab treatment schematics for adoptive transfer model; baseline Rag−/− control mice (Rag Co), baseline wildtype control mice (WT Co), pre-treatment group (Pre-Tx), isotype antibody group (Iso Ab), post treatment group (Post-Tx).

FIG. 1B depicts a comparison of DAI between Iso and TL1A Ab treated groups.

4

Figure 1A:
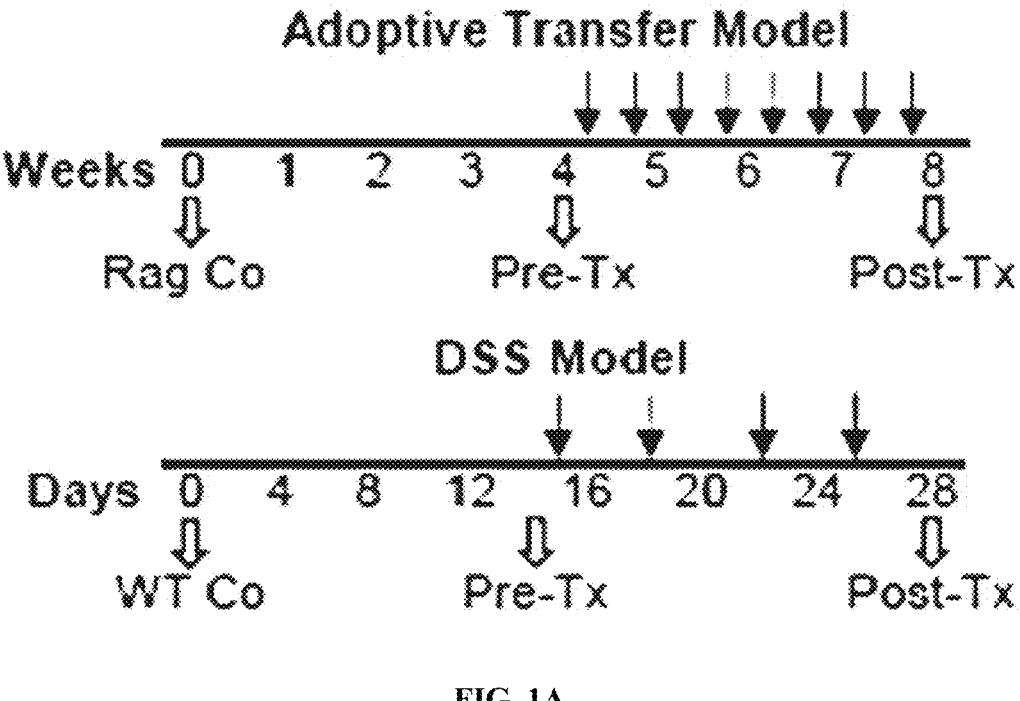
FIGS. 1A-1D depict, in accordance with an embodiment herein, TL1A Ab reduced colonic disease features.
Figure 1B:
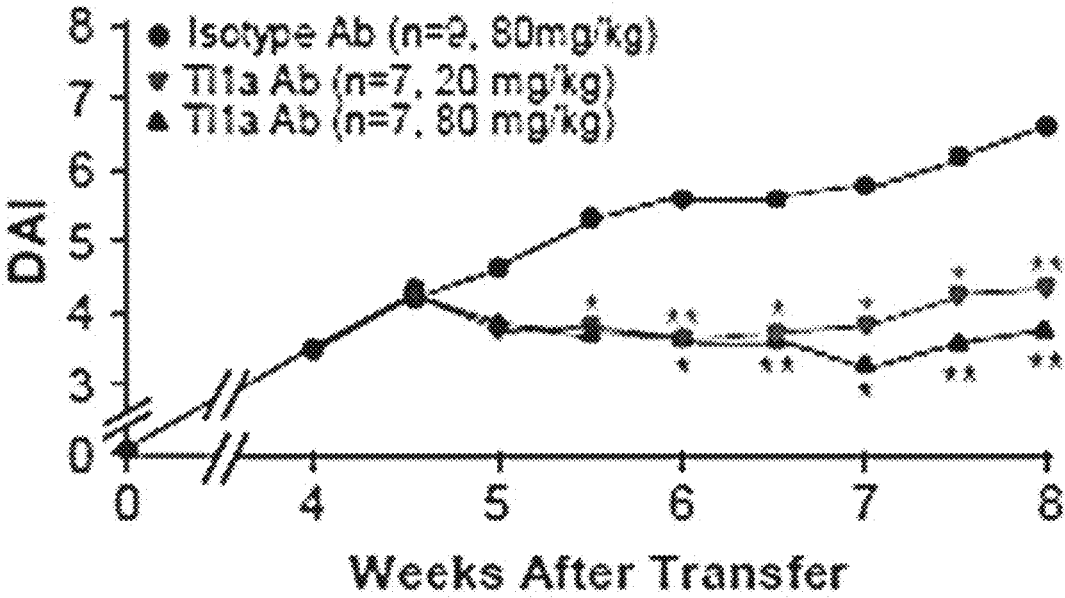
Figure 1C:
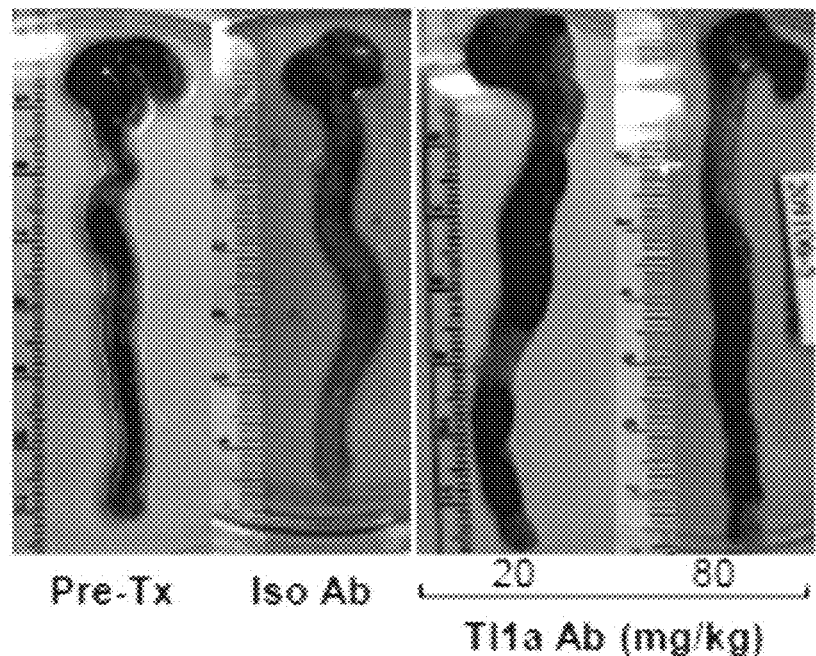
Figure 1C:
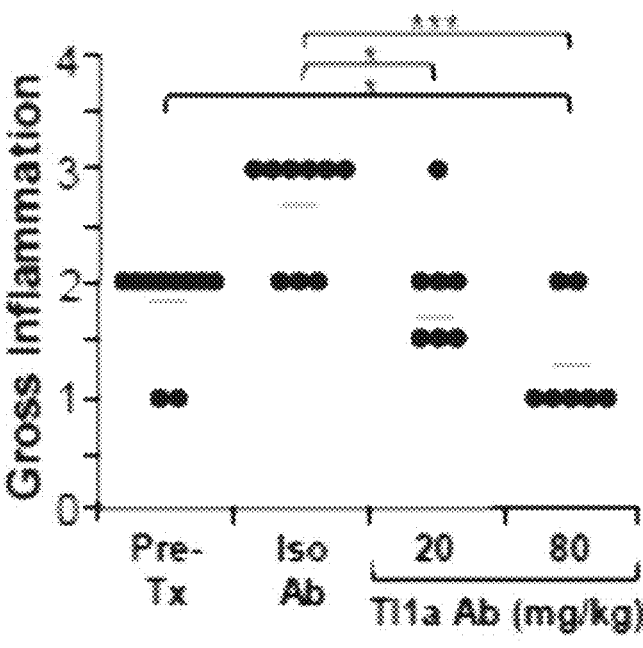

FIG. 1C depicts representative gross appearance of colon (left panels) with the quantitative inflammatory scores (right panel). Data are expressed as mean±SD.

Figure 1D:
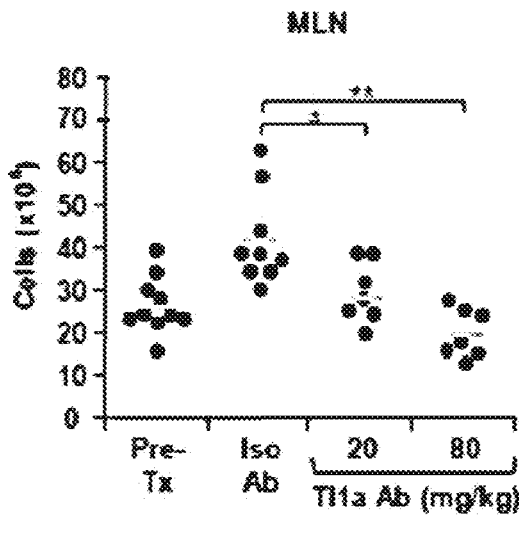
Figure 1D:
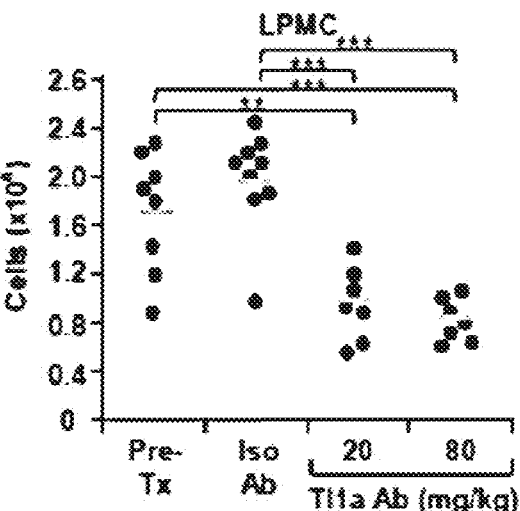

FIG. 1D depicts the total numbers of mononuclear cells isolated from MLN and LPMC. Each filled circle represents an independent mouse. TL1A Ab treated groups are compared to Pre-Tx and Iso Ab group. * p<0.05,  p<0.01, * p<0.001.

Figure 2A:
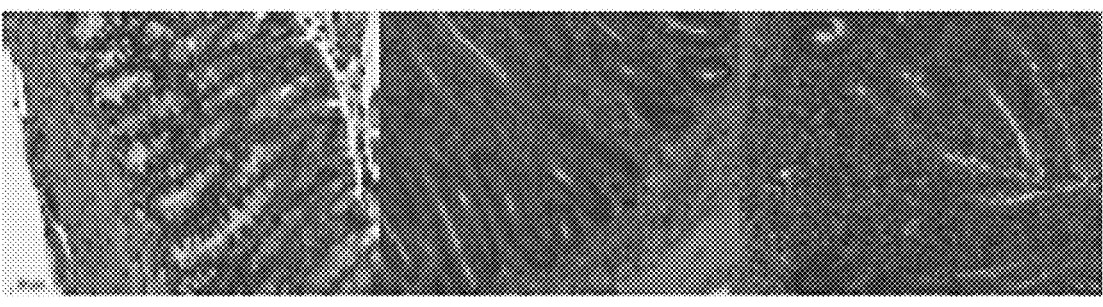
Figure 2A:
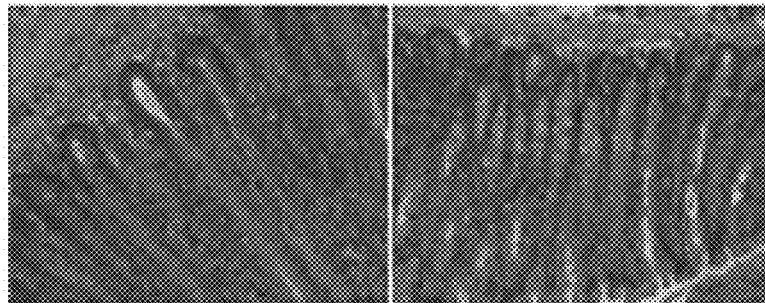
Figure 2B:
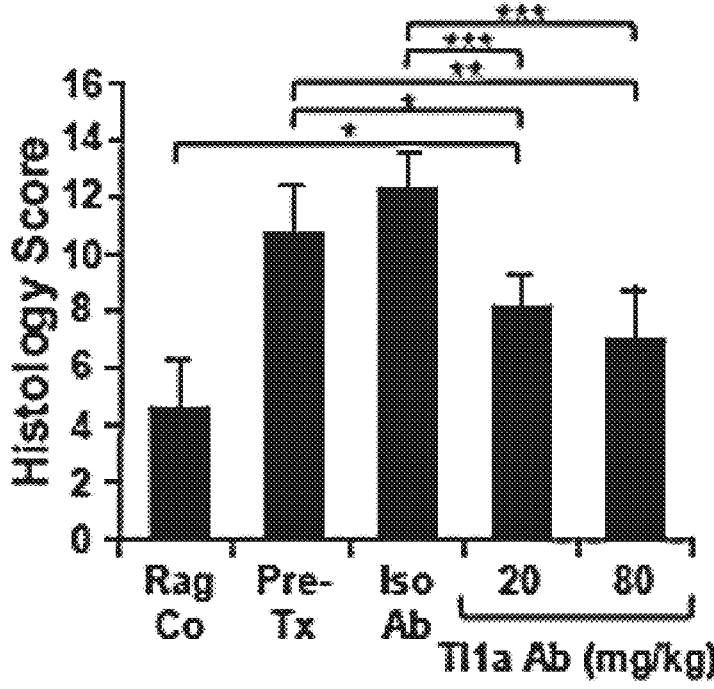
Figure 2C:
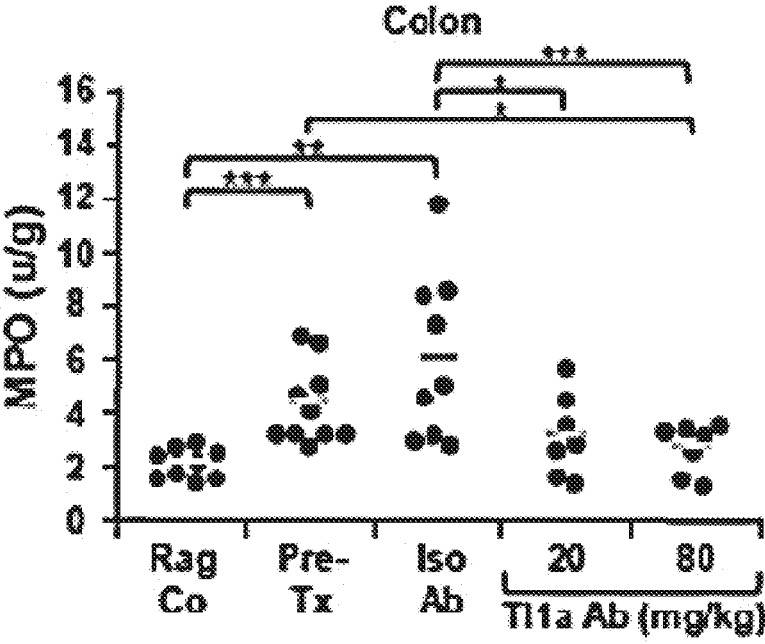

FIGS. 2A-2C depict, in accordance with an embodiment herein, TL1A Ab treatment reversed established colonic inflammation.

FIG. 2A depicts representative H&E stained mid-colon sections at 200× magnification.

FIG. 2B depicts quantitative histology scores for the adoptive transfer model. At least 20 independent fields are scored and data are expressed as mean±SD.

FIG. 2C depicts myeloperoxidase activity represented as unite of activity (u) per gram (g) of colonic protein extract. Each filled circle represents an independent mouse. TL1A Ab treated groups are compared to baseline Rag Co, Pre-Tx, and Iso Ab experimental groups. * p<0.05,  p<0.01, * p<0.001.

FIGS. 3A-3E depict, in accordance with an embodiment herein, TL1A Ab reduced Th-1 and -17 immune responses.

Figure 3A:
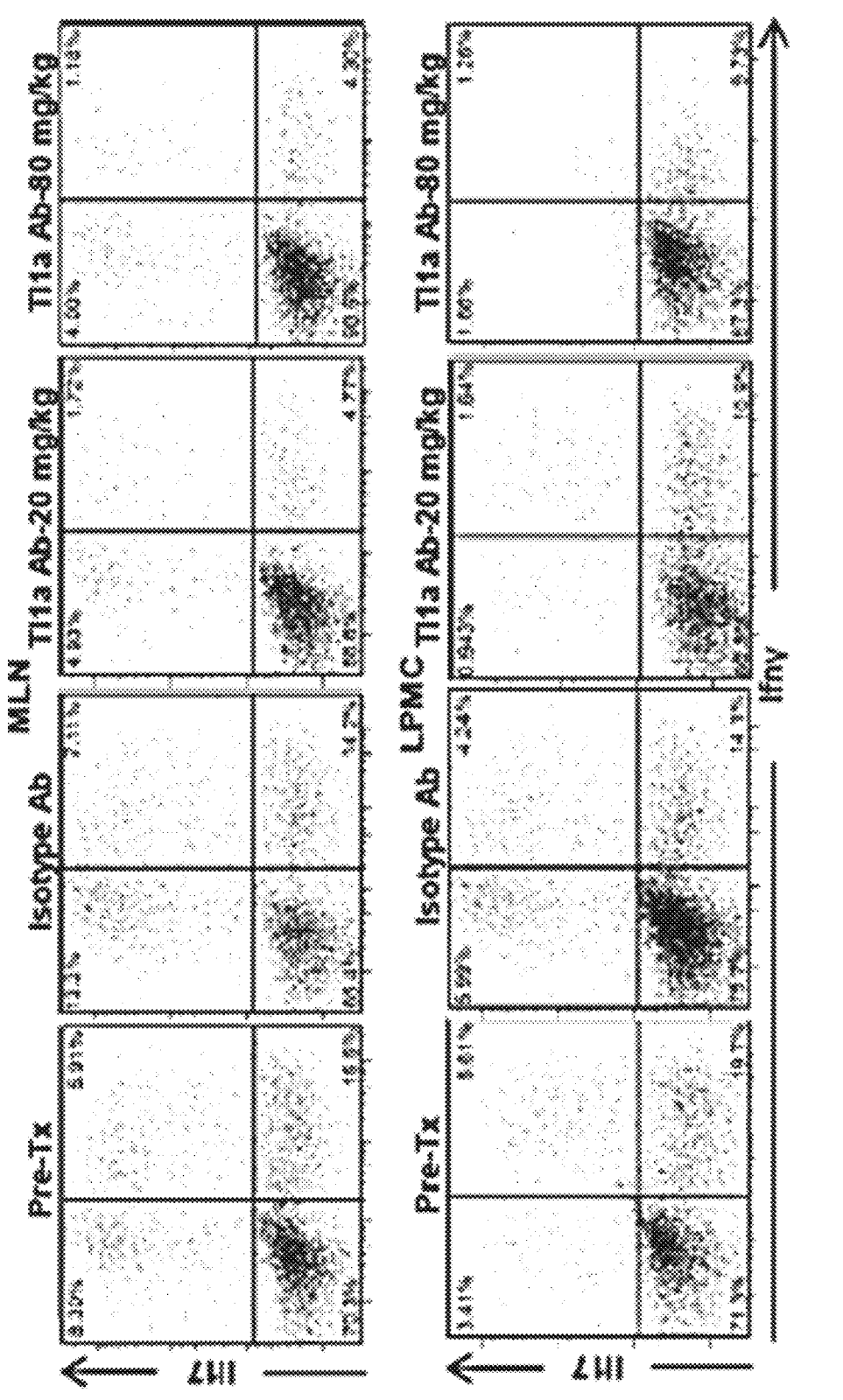

FIG. 3A depicts representative flow cytometry plots of gated CD4+ cells that were stained for intracellular Ifnγ and IL17 expression are shown for MLN (top panels) and LPMC (bottom panels).

Figure 3B:
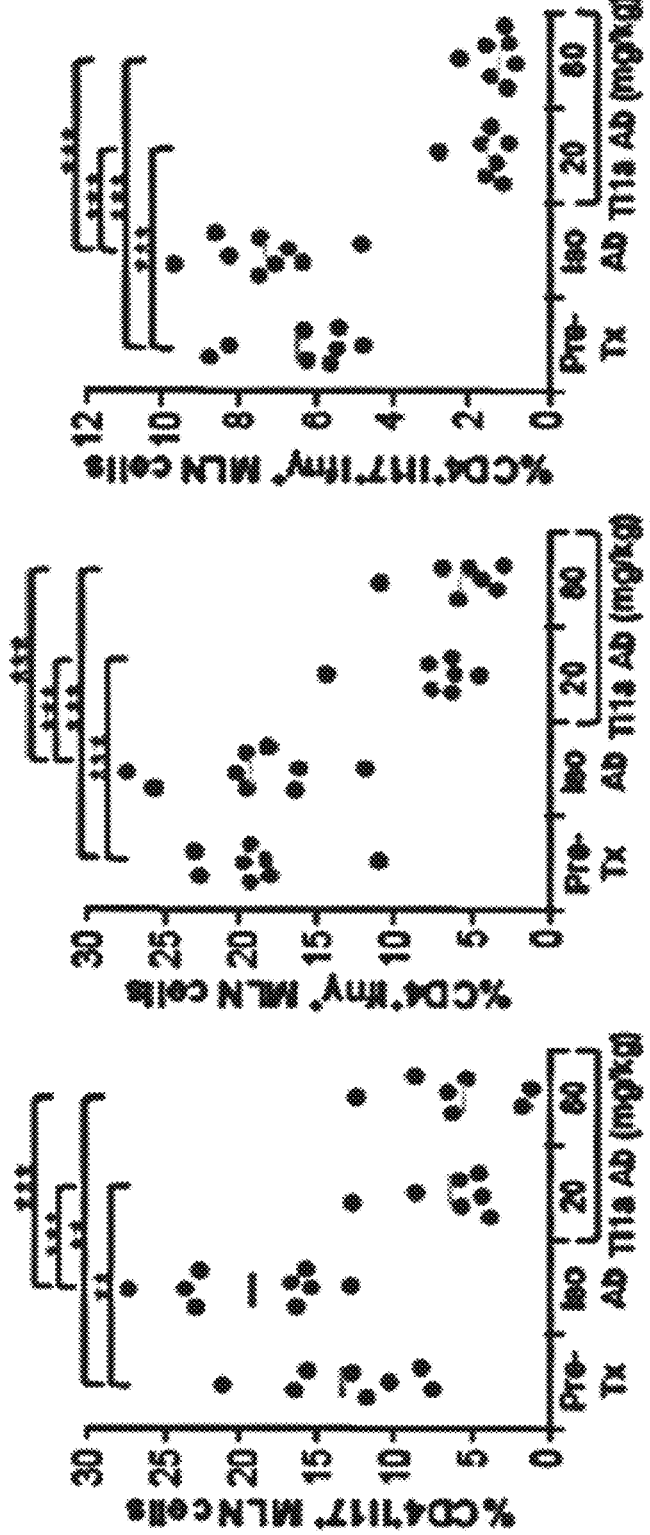
Figure 3C:
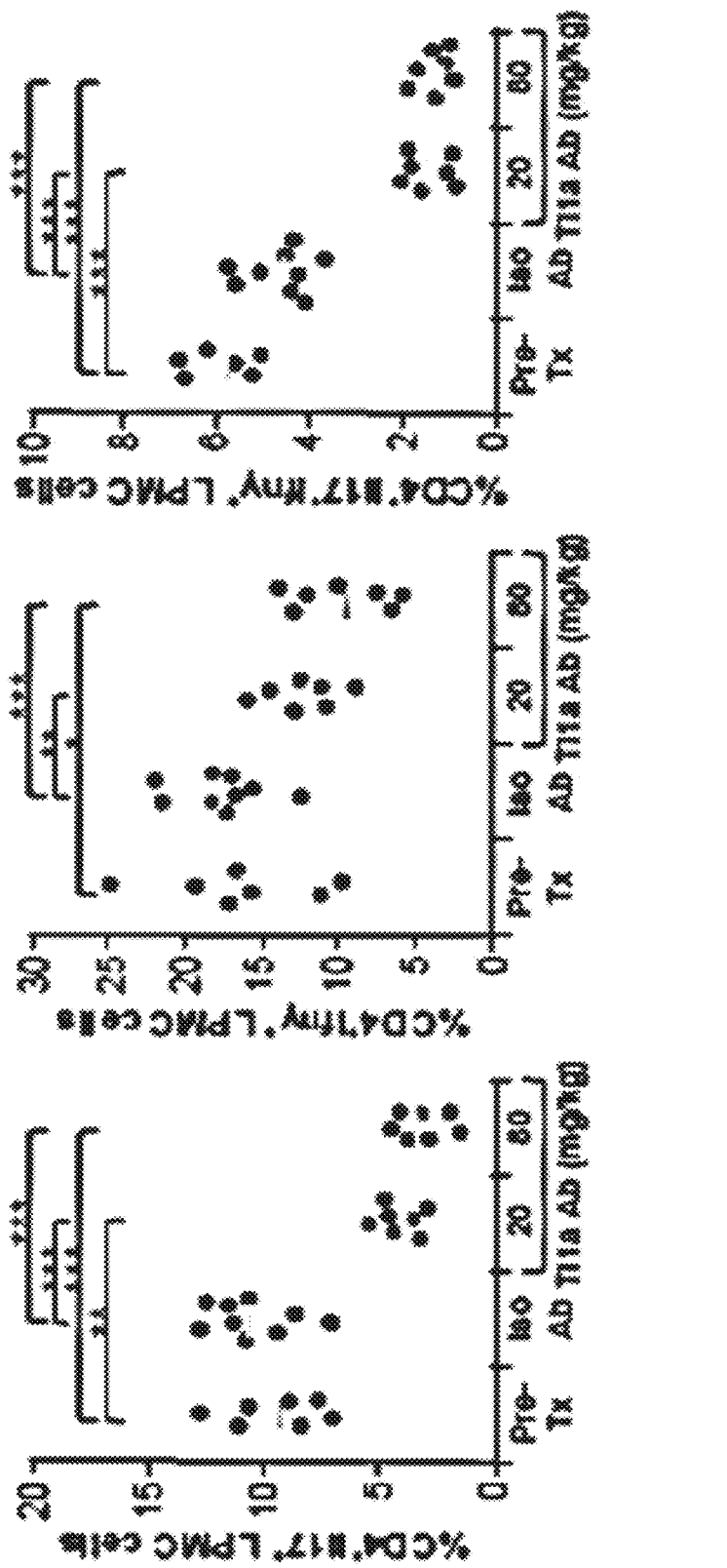

FIGS. 3B-3C depict the percentages of CD4+IL17+, CD4+Ifnγ+, and CD4+IL17+Ifnγ+ T-cells quantitated for MLN and LPMC, respectively. Each filled circle represents value obtained from an independent mouse. TL1A Ab treated groups are compared to Pre-Tx and Iso Ab experimental groups. * p<0.05,  p<0.01, * p<0.001.

Figure 3D:
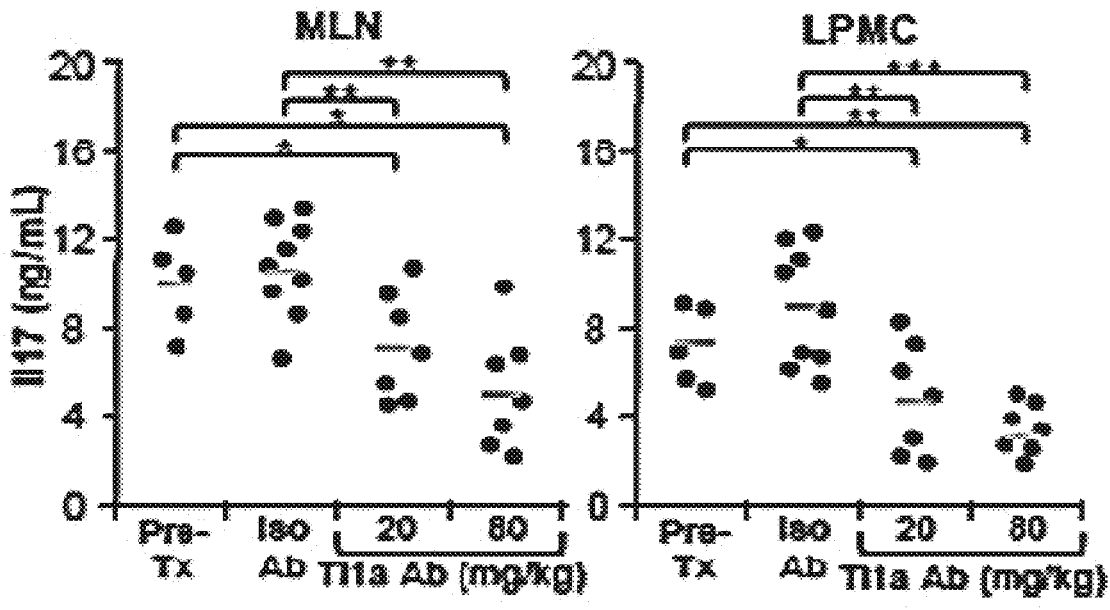
Figure 3E:
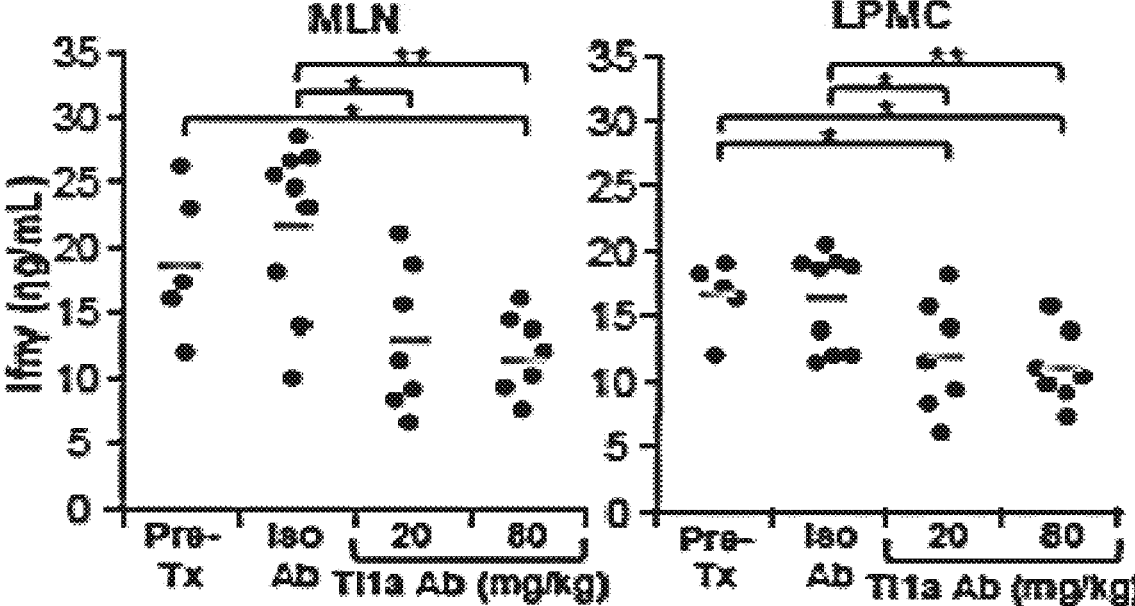

FIGS. 3D-3E depict the levels of secreted IL17 and Ifnγ, respectively. Isolated mononuclear cells from MLN and LPMC were stimulated with anti-CD3 and anti-CD28 and the levels of secreted IL17 and Ifnγ were assessed by ELISA. Each filled circle represents value obtained from an independent mouse. TL1A Ab treated groups are compared to Pre-Tx and Iso Ab experimental groups. * p<0.05,  p<0.01, * p<0.001.

FIGS. 4A-4D depict, in accordance with an embodiment herein, reversal of established fibrosis with TL1A Ab therapy in the adoptive transfer model.

Figure 4A:
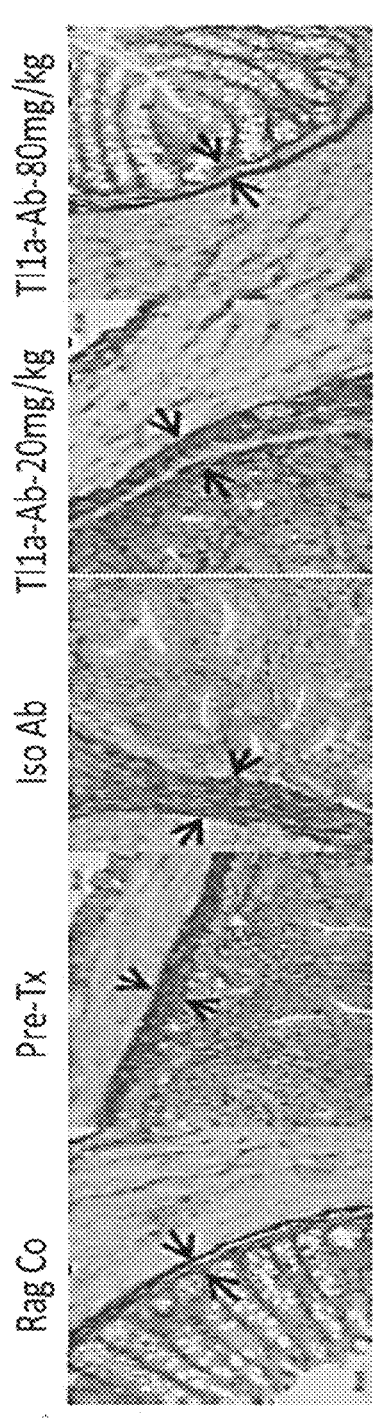

FIG. 4A depicts a representative Sirius red staining of collagen deposition in mid-colon tissue sections at 200× magnification. Black arrows denote thickness of collagen deposition.

Figure 4B:
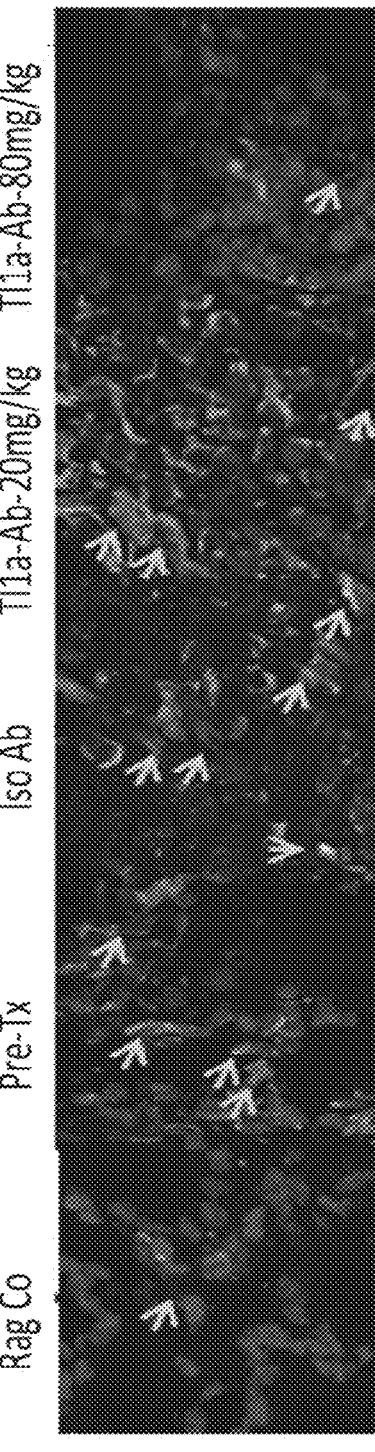

FIG. 4B depicts a representative immunofluorescent staining of vimentin (green) and αSMA (red) from mid-colon sections are shown. Orange arrows denote myofibroblast that coexpresses vimentin and αSMA.

Figure 4C:
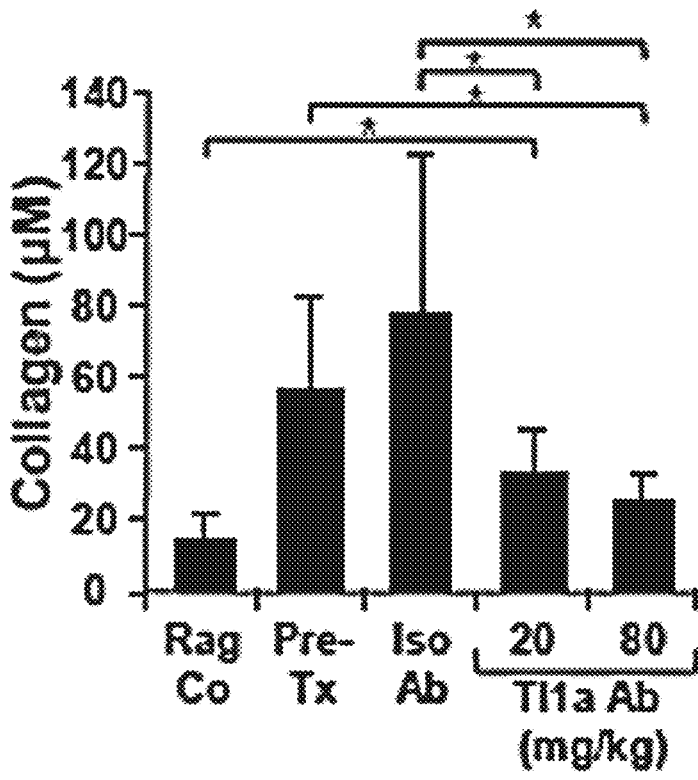

FIG. 4C depicts the quantitation of the collagen thickness from the mid-colon sections expressed as mean±SD. At least 20 independent fields were scored per group. TL1A Ab treated groups are compared to baseline Rag Co, Pre-Tx, and Iso Ab experimental groups. * p<0.05,  p<0.01, * p<0.001.

Figure 4D:
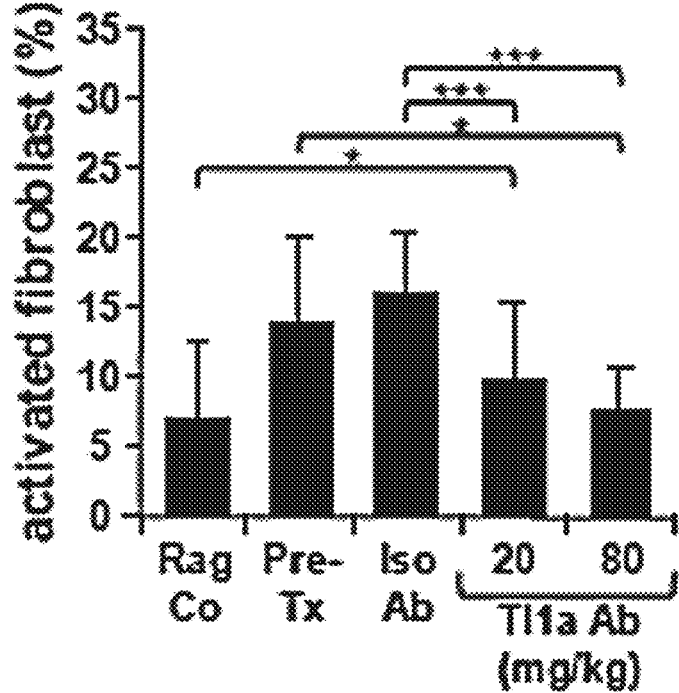

FIG. 4D depicts the percentages of activated fibroblasts from the mid-colon sections expressed as mean±SD. At least 20 independent fields were scored per group. TL1A Ab treated groups are compared to baseline Rag Co, Pre-Tx, and Iso Ab experimental groups. * p<0.05,  p<0.01, * p<0.001.

FIGS. 5A-5D depict, in accordance with an embodiment herein, reduced proliferation of intestinal fibroblasts with DR3 deficiency.

Figures 5A, 5B:
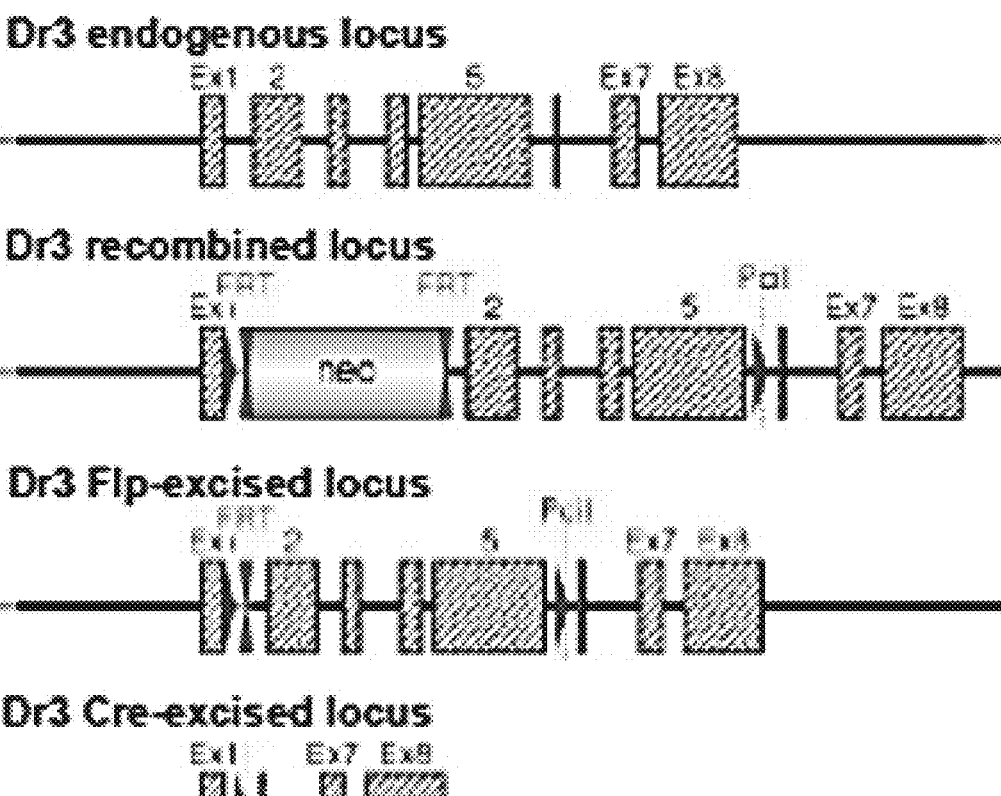

FIG. 5A depicts a schematic representation of mouse DR3 endogenous locus and strategy for gene targeting.

FIG. 5B depicts a representative polymerase chain reaction for DR3 genotype shown with targeted (DR3 KO) band running at 506 bp and endogenous DR3 locus running at 353 bp.

Figures 5C, 5D:
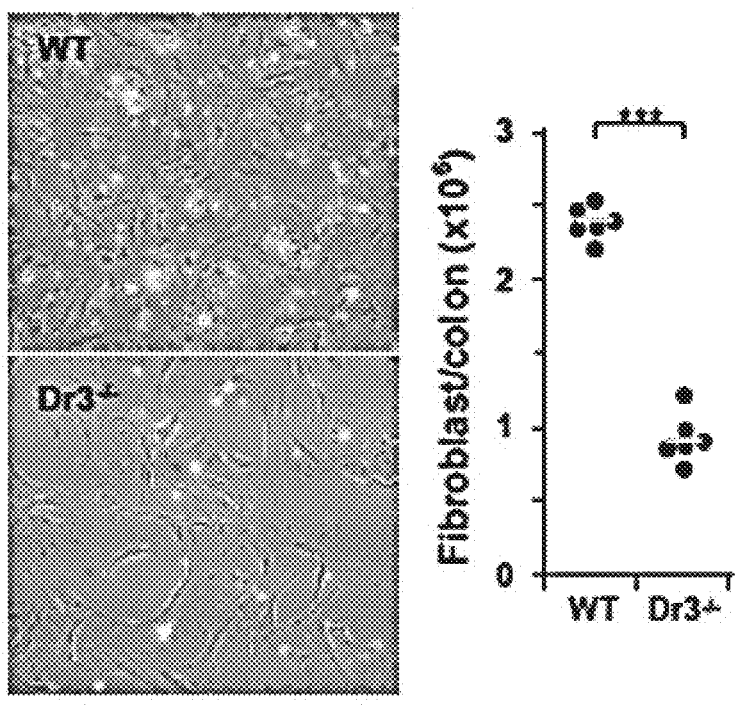

FIG. 5C depicts a representative panel of 6 photographs of intestinal fibroblasts recovered from littermate WT and DR3−/− colon (left panels) and individual total fibroblasts per colon is plotted (right panel).

FIG. 5D depicts representative flow cytometric histograms showing the quantification of proliferating fibroblasts (top panel) and fibroblasts undergoing apoptosis (bottom panel) from WT and DR3−/− mice. Decreased CellTrace violet fluorescence intensity indicates proliferation. Increased Annexin V staining indicates apoptosis. Shown are representative flow cytometric histograms of at least 6 independent experiments with similar results. *** p<0.001.

FIGS. 6A-6D depict, in accordance with an embodiment herein, intestinal fibroblasts express DR3 and respond to TL1A stimulation.

Figure 6A:
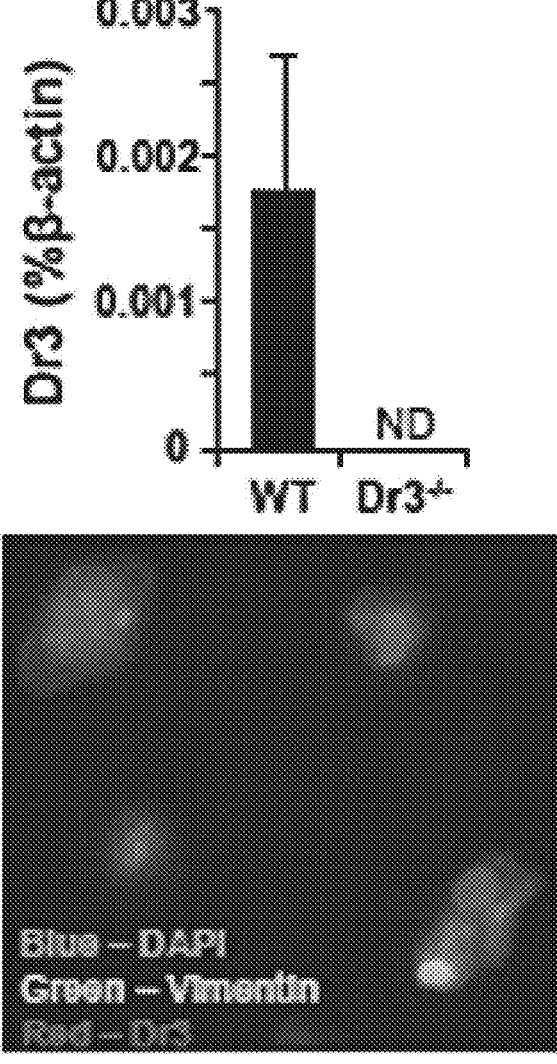

FIG. 6A depicts DR3 mRNA detection in WT but not DR3−/− fibroblasts (top). ND=not detected. An immunofluorescent staining of WT fibroblasts showed positive DR3 staining in red (bottom).

Figure 6B:
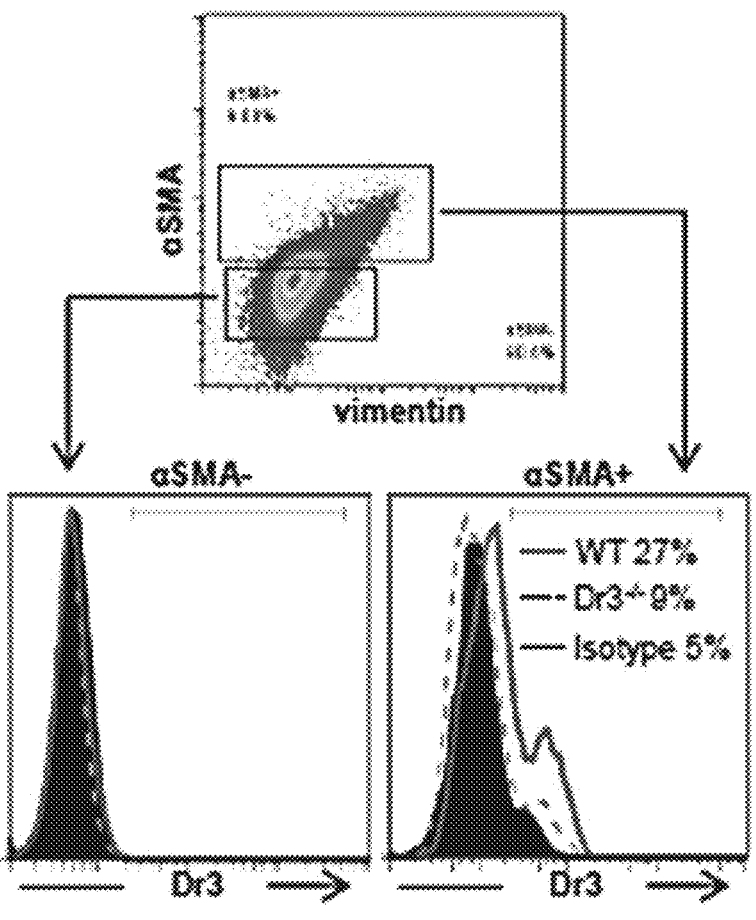

FIG. 6B depicts a representative flow cytometric histogram of primary intestinal fibroblasts stained with DR3, αSMA and vimentin. αSMA positive and negative fibroblasts were gated as shown and DR3 staining is found in αSMA+ WT but not DR3−/− and αSMA negative cells. Data shown are representative of at least 3 independent experiments with similar results.

Figure 6C:
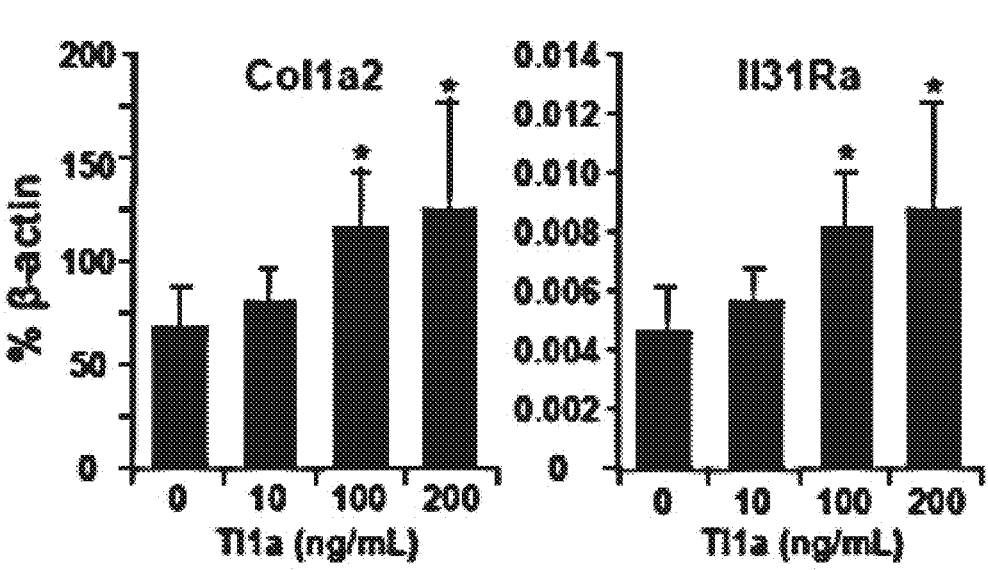

FIG. 6C depicts the expression of Col1a2 and IL31Ra mRNA in WT primary intestinal fibroblasts with increasing TL1A stimulation (0-200 ng/mL) and represented as mean±SD.

Figure 6D:
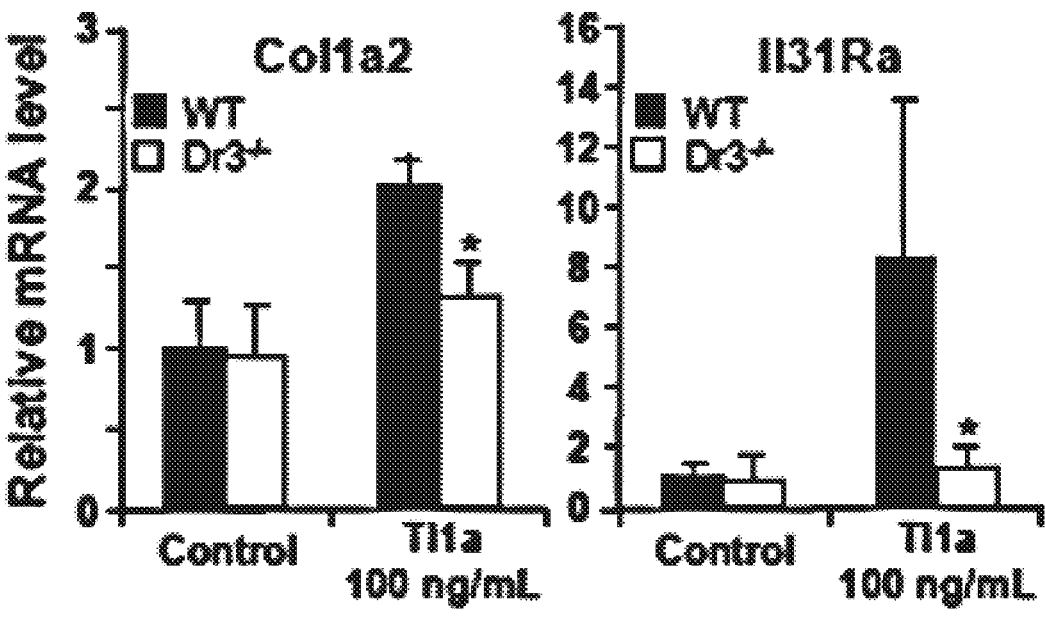

FIG. 6D depicts the relative induction of Col1a2 and IL31Ra mRNA by TL1A in WT and DR3−/− intestinal and represented as mean±SD. * p<0.05.

Figure 7A:
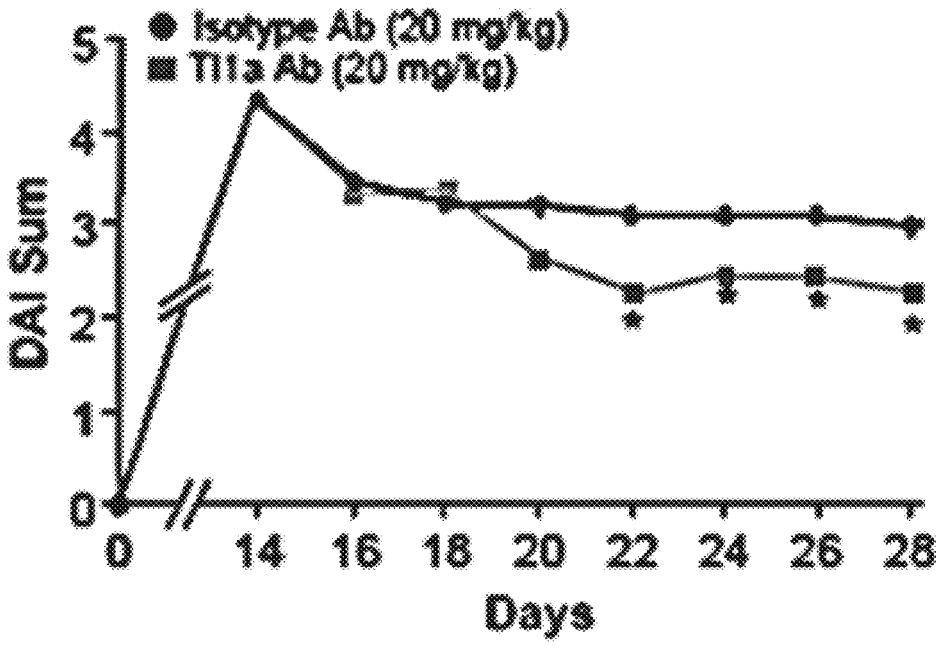
Figure 7B:
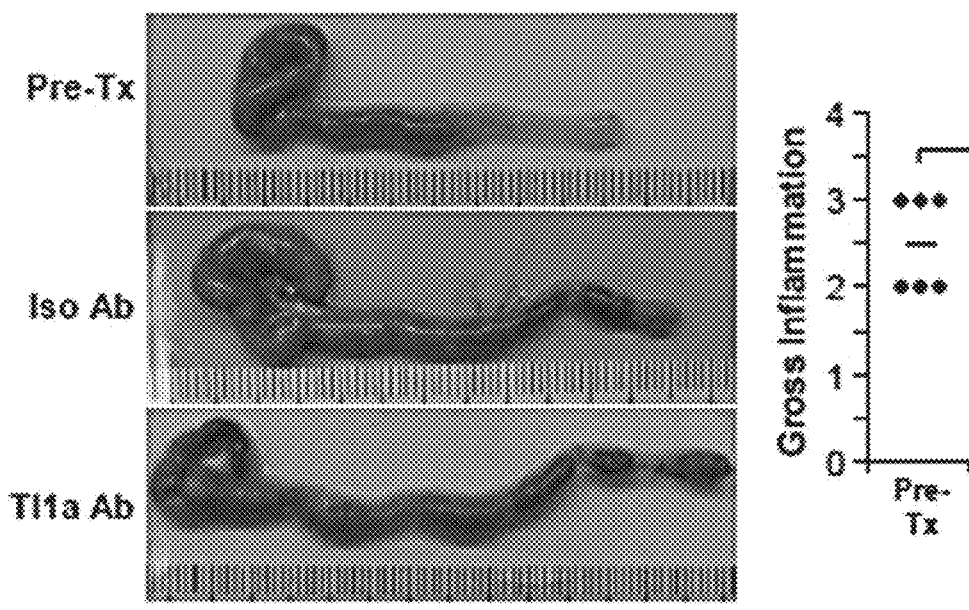
Figure 7C:
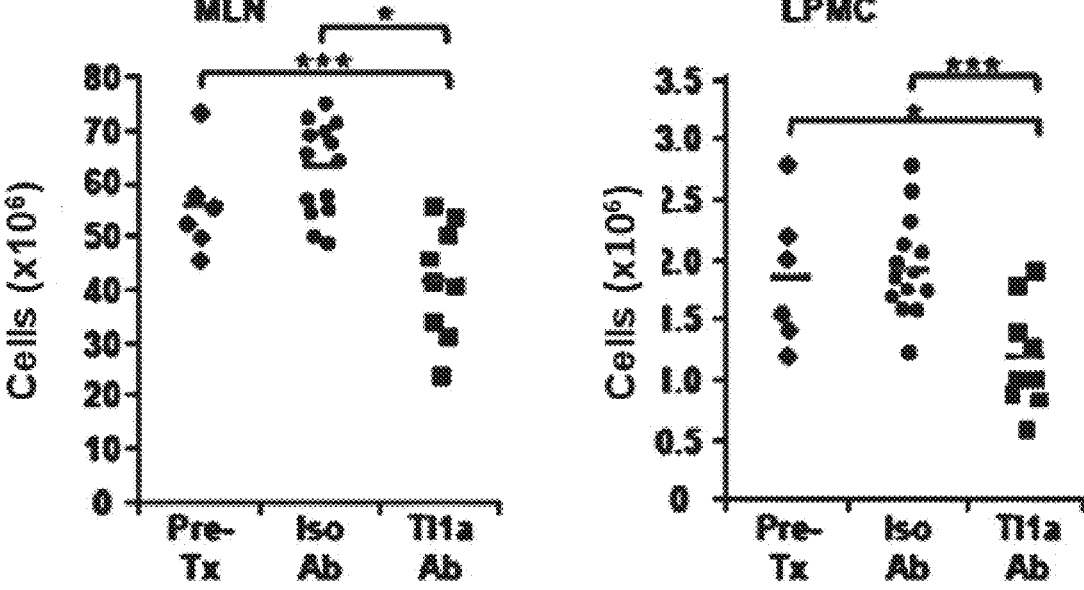

FIGS. 7A-7C depict, in accordance with an embodiment herein, TL1A Ab reduced inflammatory disease activity due to chronic DSS administration.

FIG. 7A compares the DAI between isotype Ab (n=14) and TL1A Ab (n=9) treated groups.

FIG. 7B depicts the representative gross appearance of colon (left panels) with the quantitative inflammatory score (right panel). Data are expressed as mean±/−SD. Each filled symbol represents an independent mouse. TL1A Ab treated groups are compared to Pre-Tx and Iso Ab group. * P<0.05,  P<0.01, * P<0.001.

FIG. 7C depicts the total numbers of mononuclear cells isolated from MLN and LP. Each filled symbol represents an independent mouse. TL1A Ab treated groups are compared to Pre-Tx and Iso Ab group. * P<0.05,  P<0.01, * P<0.001.

Figure 8A:
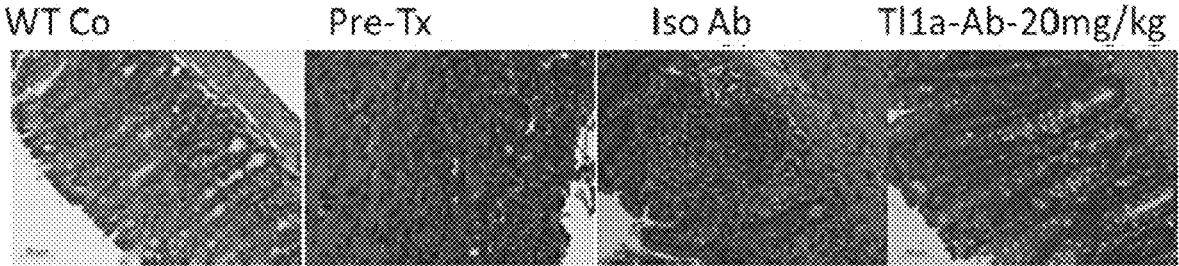
Figure 8B:
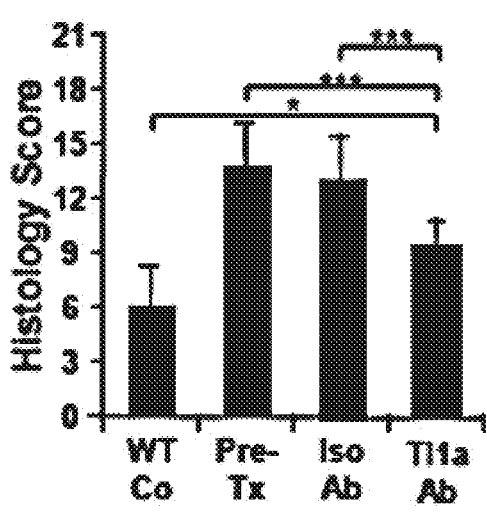
Figure 8C:
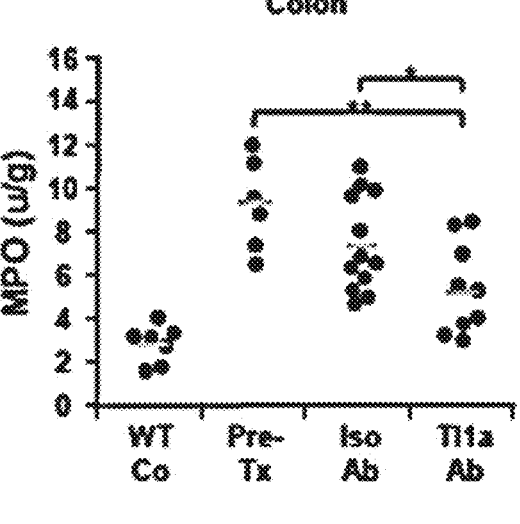

FIGS. 8A-8C depict, in accordance with an embodiment herein, TL1A Ab reversed established colonic inflammation in the chronic DSS model.

FIG. 8A depicts representative H&E stained mid-colon sections at 200× magnification.

FIG. 8B depicts quantitation of histologic inflammation from at least 20 in dependent mid-colon fields are scored and data are expressed as mean±/−SD . . . * P<0.05,  P<0.01, * P<0.001.

FIG. 8C depicts myeloperoxidase activity as unit of activity (u) per gram (g) of colonic protein extract. TL1A Ab treated groups are compared to baseline WT Co, Pre-Tx, and Iso Ab experimental groups. Each filled circle represent MPO activity from an independent colon. * P<0.05,  P<0.01, * P<0.001.

FIGS. 9A-9E depict, in accordance with an embodiment herein, TL1A Ab reduced Th-1 and -17 immune responses in the chronic DSS colitis model.

Figure 9A:
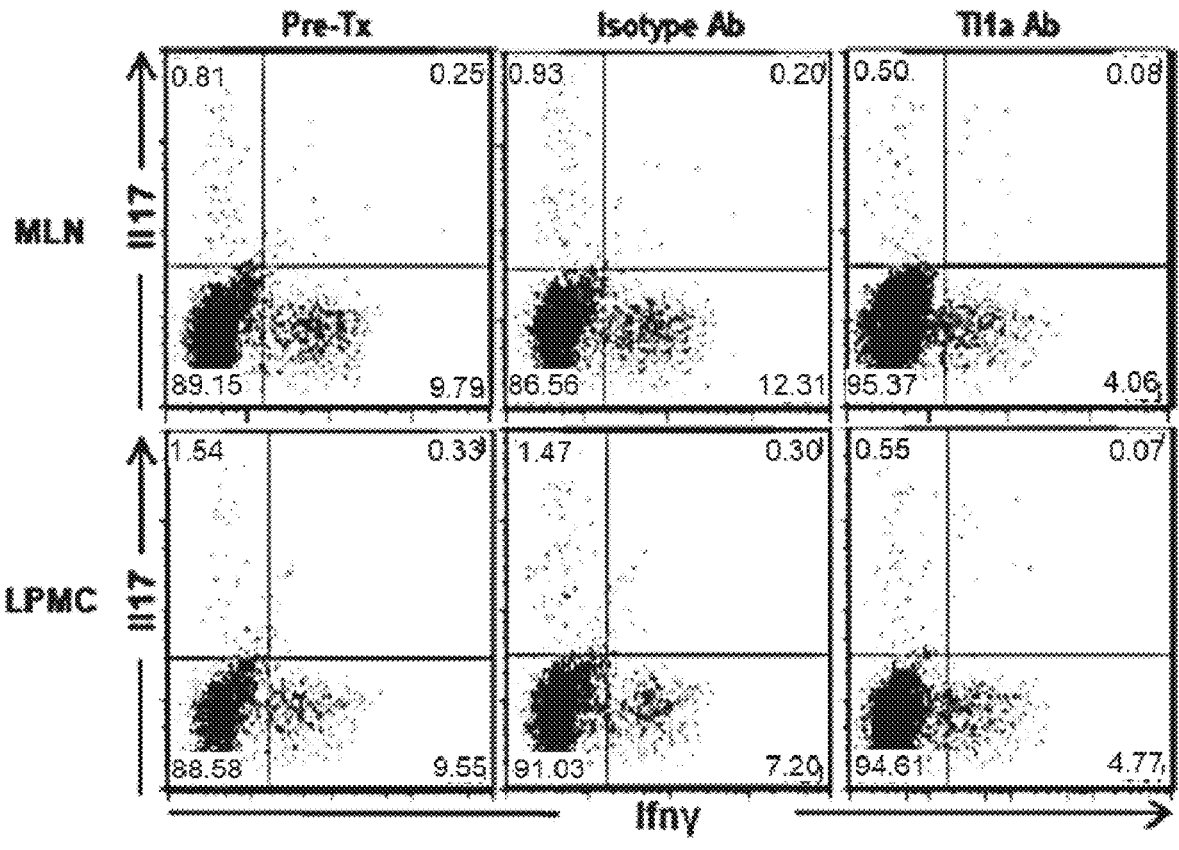

FIG. 9A depicts representative flow cytometry plots of gated CD4+ cells from (top panels) and LPMC (bottom panels) that were stained for intracellular Ifnγ and IL-17.

Figure 9B:
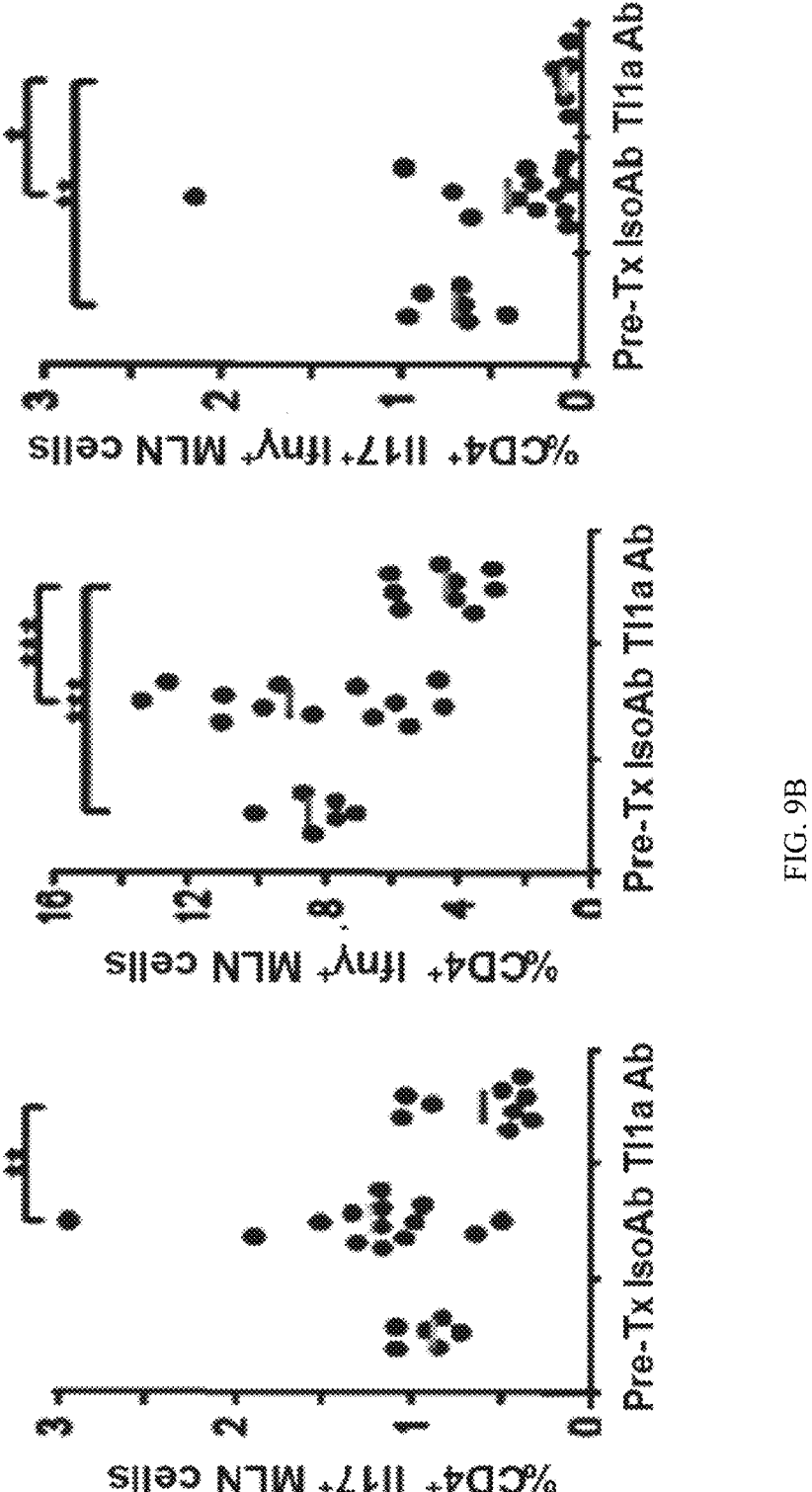
Figure 9C:
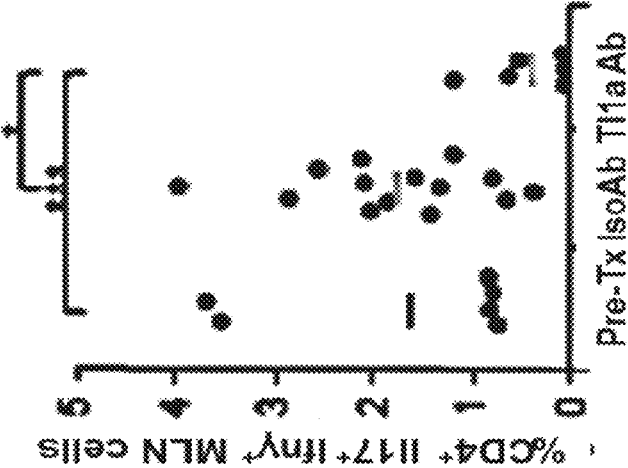
Figure 9C:
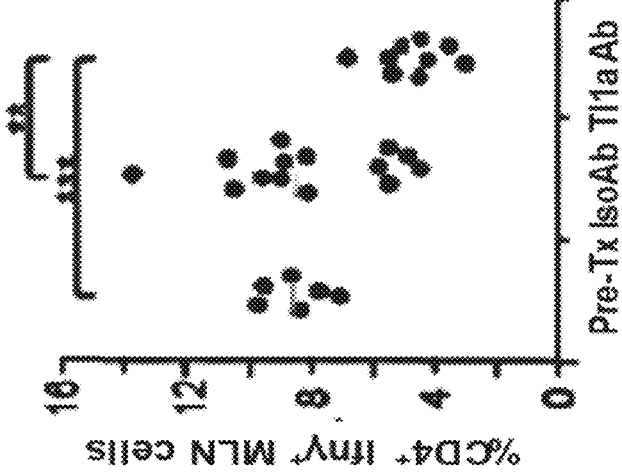
Figure 9C:
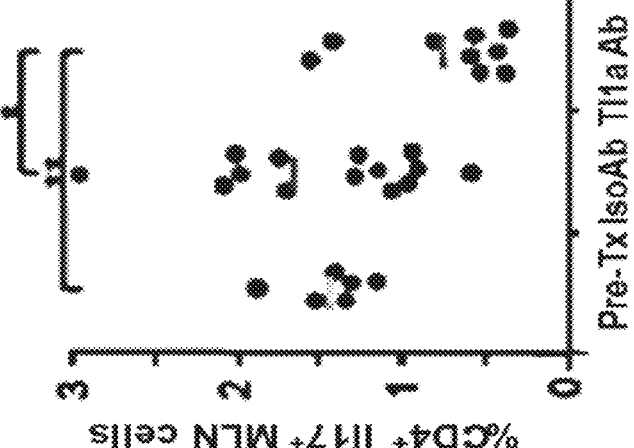

FIGS. 9B-9C depict the percentages of CD4+IL17+, CD4+Ifnγ+, and CD4+IL17+Ifnγ+ T-cells for MLN and LPMC, respectively. Each filled circle represents value obtained from an independent mouse. * p<0.05,  p<0.01, * p<0.001.

Figure 9D:
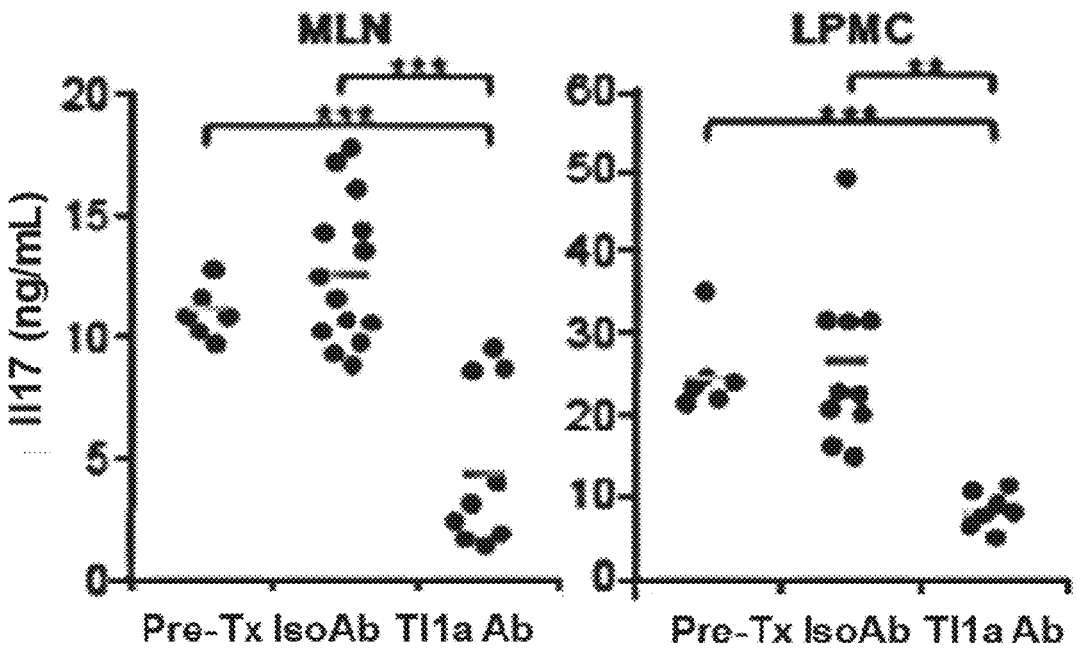
Figure 9E:
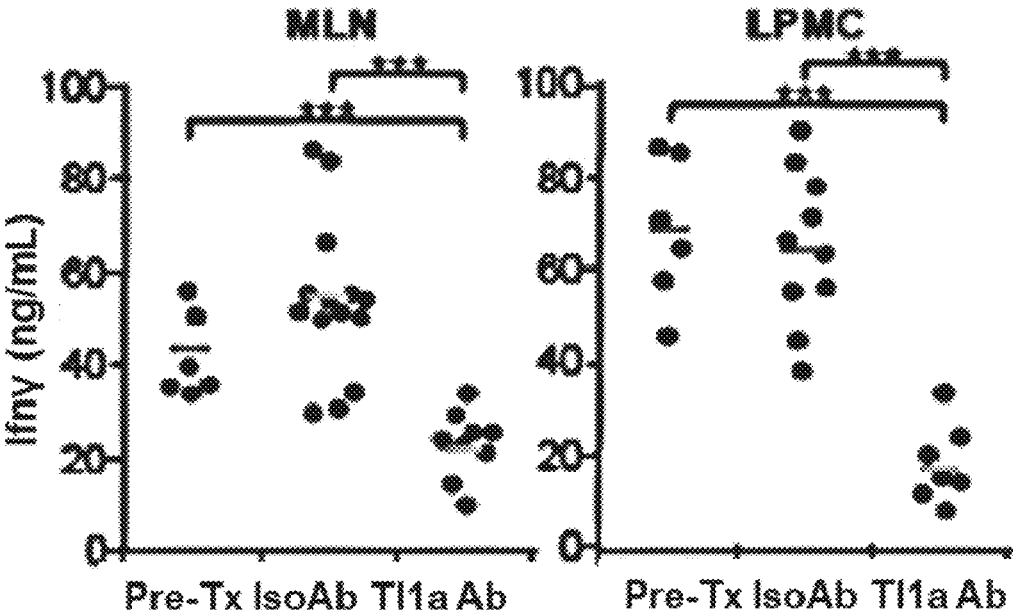

FIGS. 9D-9E depict levels of secreted IL17 and Ifnγ, respectively in isolated mononuclear cells from MLN and LPMC stimulated with anti-CD38 and anti-CD28. Each filled circle represents value obtained from an independent mouse. * p<0.05,  p<0.01, * p<0.001.

FIGS. 10A-10D depict, in accordance with an embodiment herein, reversal of established fibrosis with TL1A Ab in the chronic DSS colitis model.

Figure 10A:
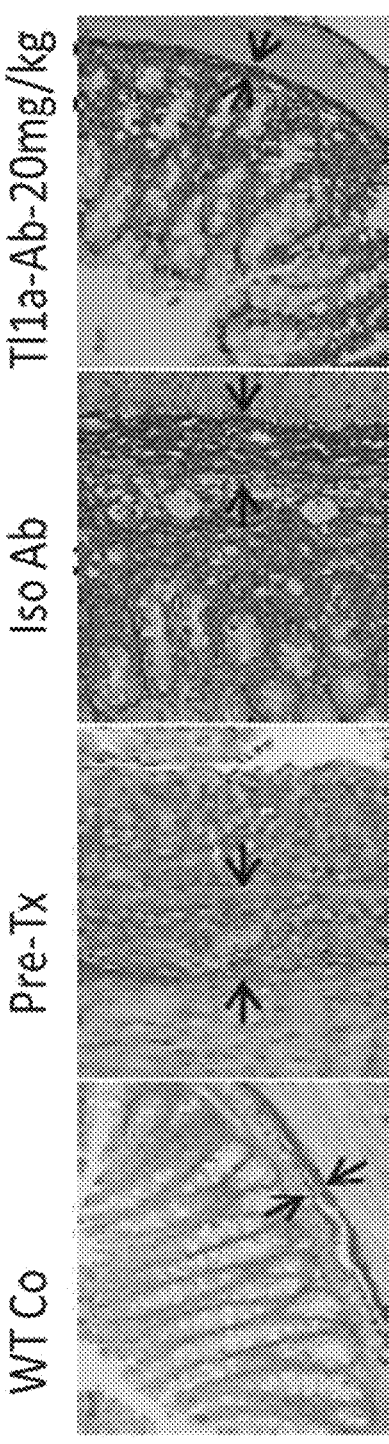

FIG. 10A depicts representative Sirius red staining of collagen deposition in mid-colon tissue sections at 200× magnification. Black arrows denote thickness of collagen deposition.

Figure 10B:
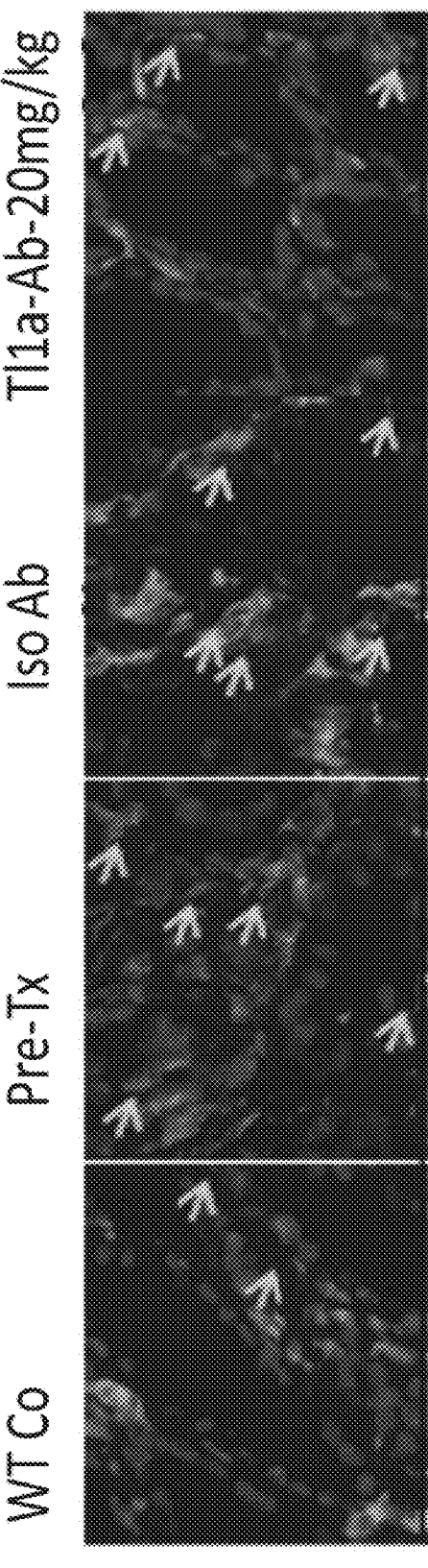

FIG. 10B depicts representative immunofluorescent staining of vimentin (green) and αSMA (red) from mid-colon sections are shown. Orange arrows denote myofibroblast that co-expresses vimentin and αSMA.

Figure 10C:
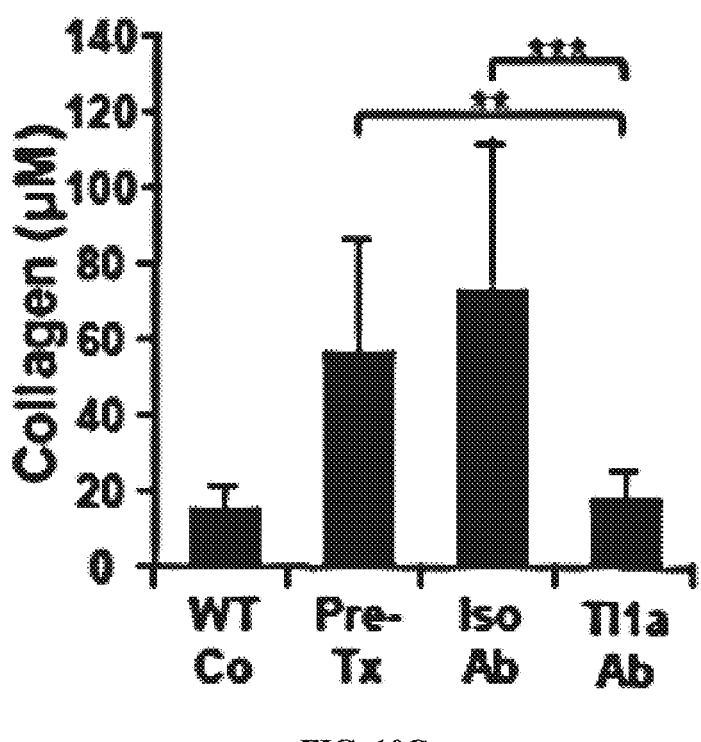
Figure 10D:
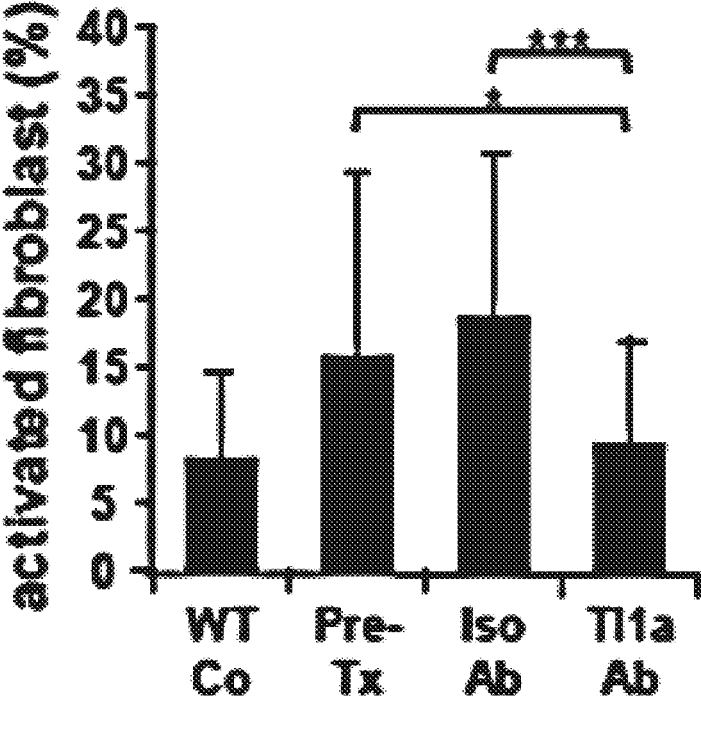

FIGS. 10C-10D depict quantitation of the collagen thickness and percentages of activated fibroblasts, respectively, from the mid-colon sections expressed as mean±SD. At least 20 independent fields were scored per group. * p<0.05,  p<0.01, * p<0.001.

FIGS. 11A-11F depict, in accordance with an embodiment herein, TL1A Ab reduced myofibroblast number and expression of DR3 and 1.

Figure 11A:
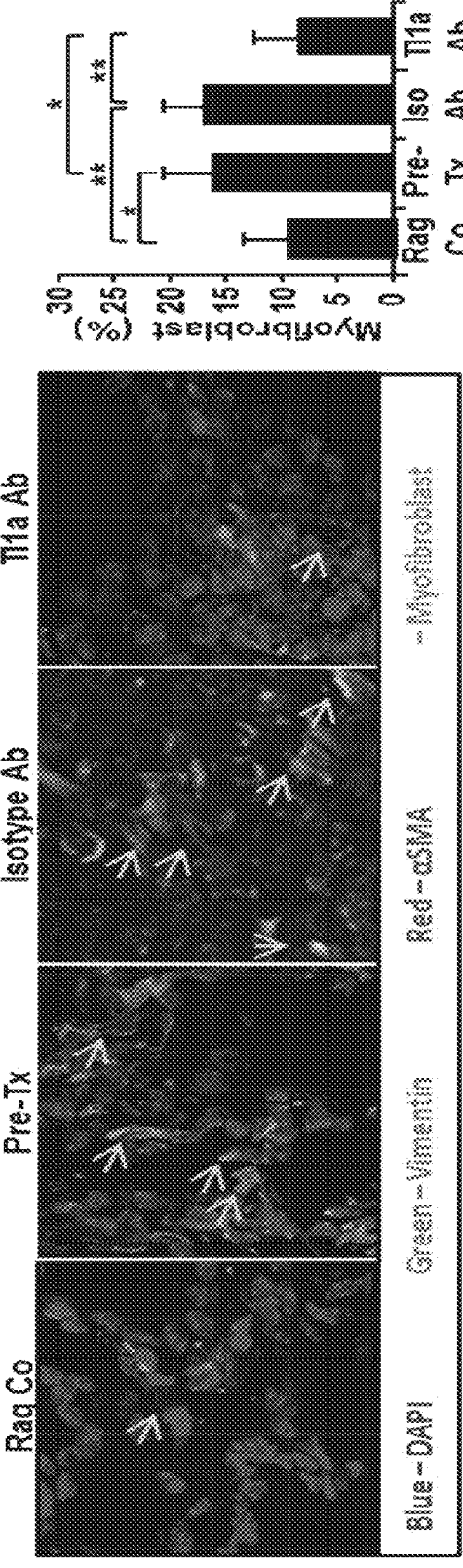
Figure 11B:
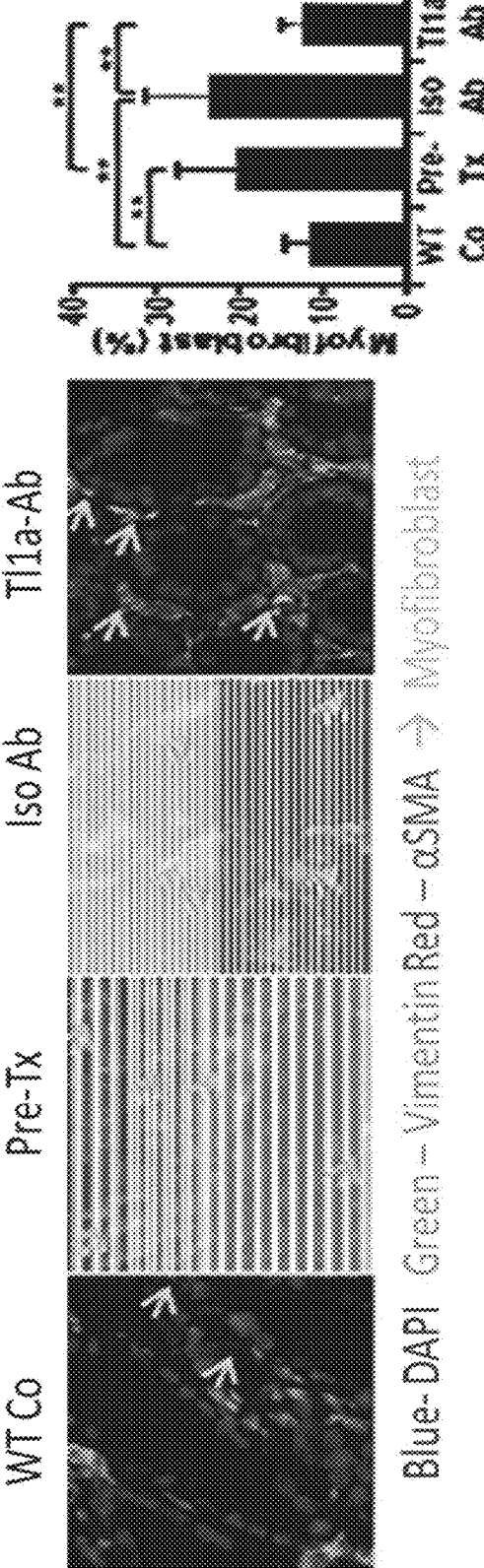

FIGS. 11A-11B depict a representative immunofluorescent staining of vimentin (green) and αSMA (red) from mid-colon sections from the adoptive transfer model and chronic DSS model, respectively, at 630× magnification. Orange arrows denote myofibroblasts that co-express vimentin and αSMA. Percentages of myofibroblasts from the mid-colon sections were quantitated and expressed as mean±SD for the adoptive transfer model (FIG. 11A, right panel) and chronic DSS model (FIG. 11B, right panel). At least 10 independent fields were scored per group.

Figure 11C:
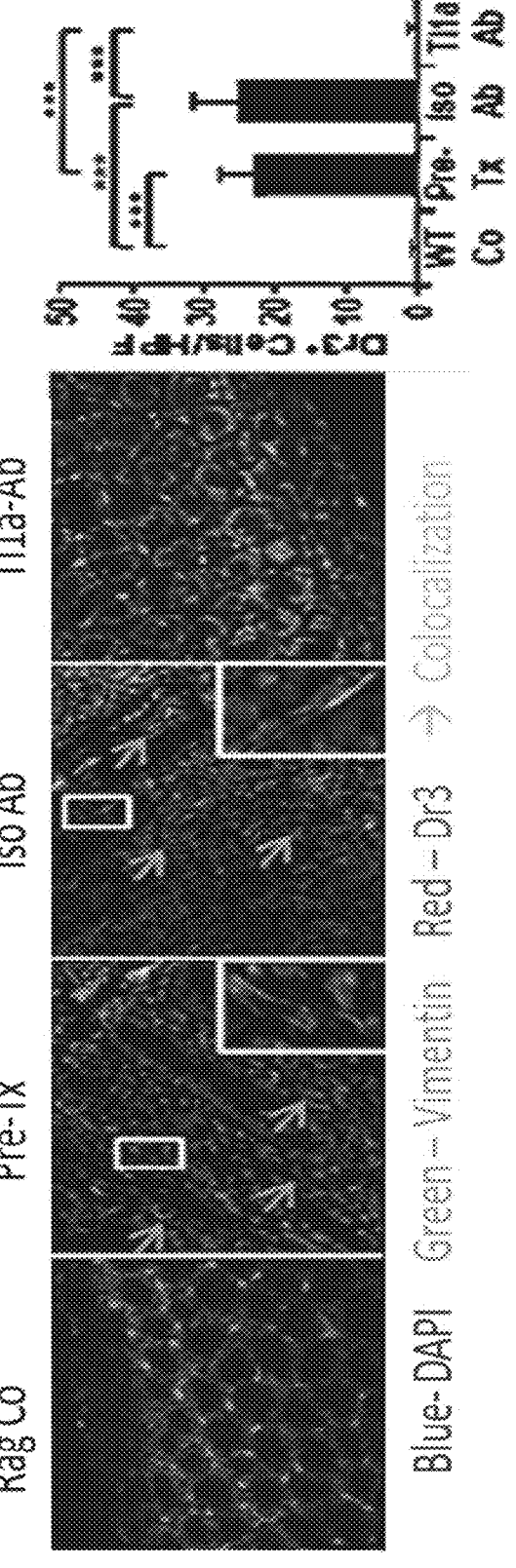
Figure 11D:
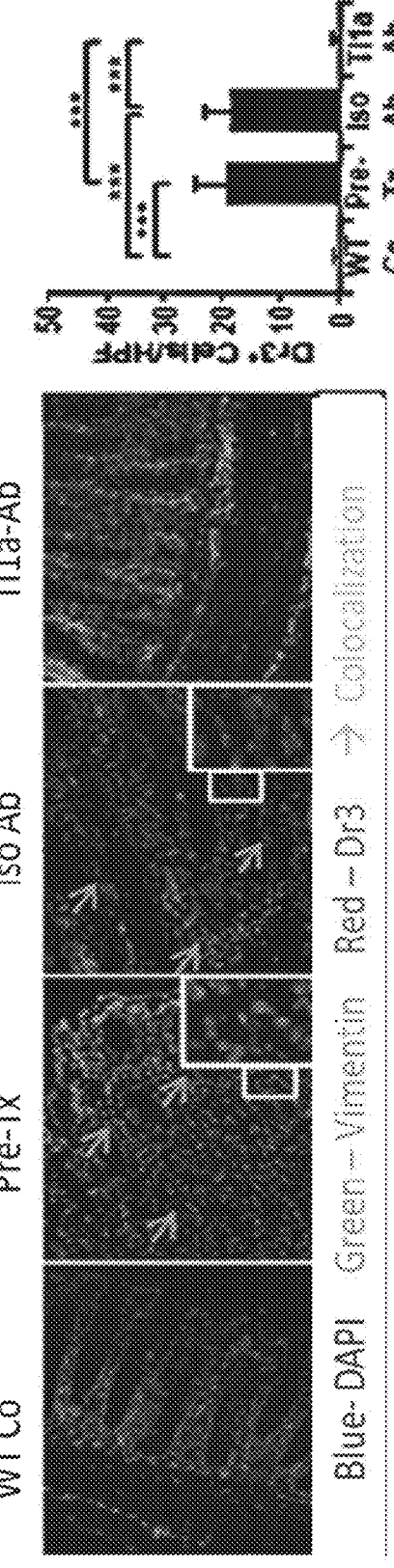

FIGS. 11C-11D depict representative immunofluorescent staining of vimentin (green) and DR3 (red) from mid-colon sections from the adoptive transfer model and chronic DSS model, respectively. Figure insets are larger view of the images that were acquired at 200× magnification. At least 8 independent fields were quantitated per group and plotted as DR3+ cells per high power fields (HPF). Specifically, FIGS. 11C-11D show increased DR3 staining on fibroblasts in the Pre-treatment and Isotype antibody group (both associated with higher collagen deposition) as compared to TL1A Ab treatment group (associated with lower collagen deposition).

Figures 11E, 11F:
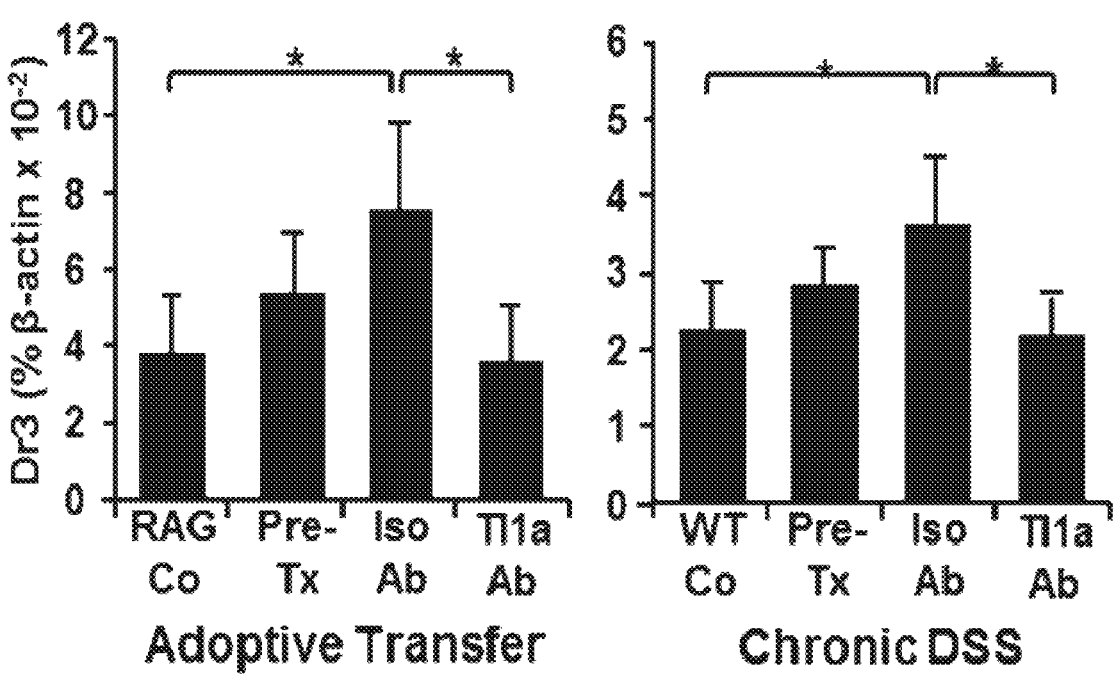

FIGS. 11D-11E depict quantification of colonic DR3 and TL1A mRNA, respectively, as mean±SD (n=5-14). TL1A Ab treated groups are compared to baseline Rag Co, Wt Co, Pre-Tx, and Iso Ab experimental groups. * P<0.05,  P<0.01, * P<0.001. Specifically, FIGS. 11E-11F show by RT-PCR expression analysis that both TL1A and DR3 expression is downregulated in the TL1A Ab group (associated with lower collagen deposition) as compared to isotype group (associated with higher collagen deposition).

Figure 12A:
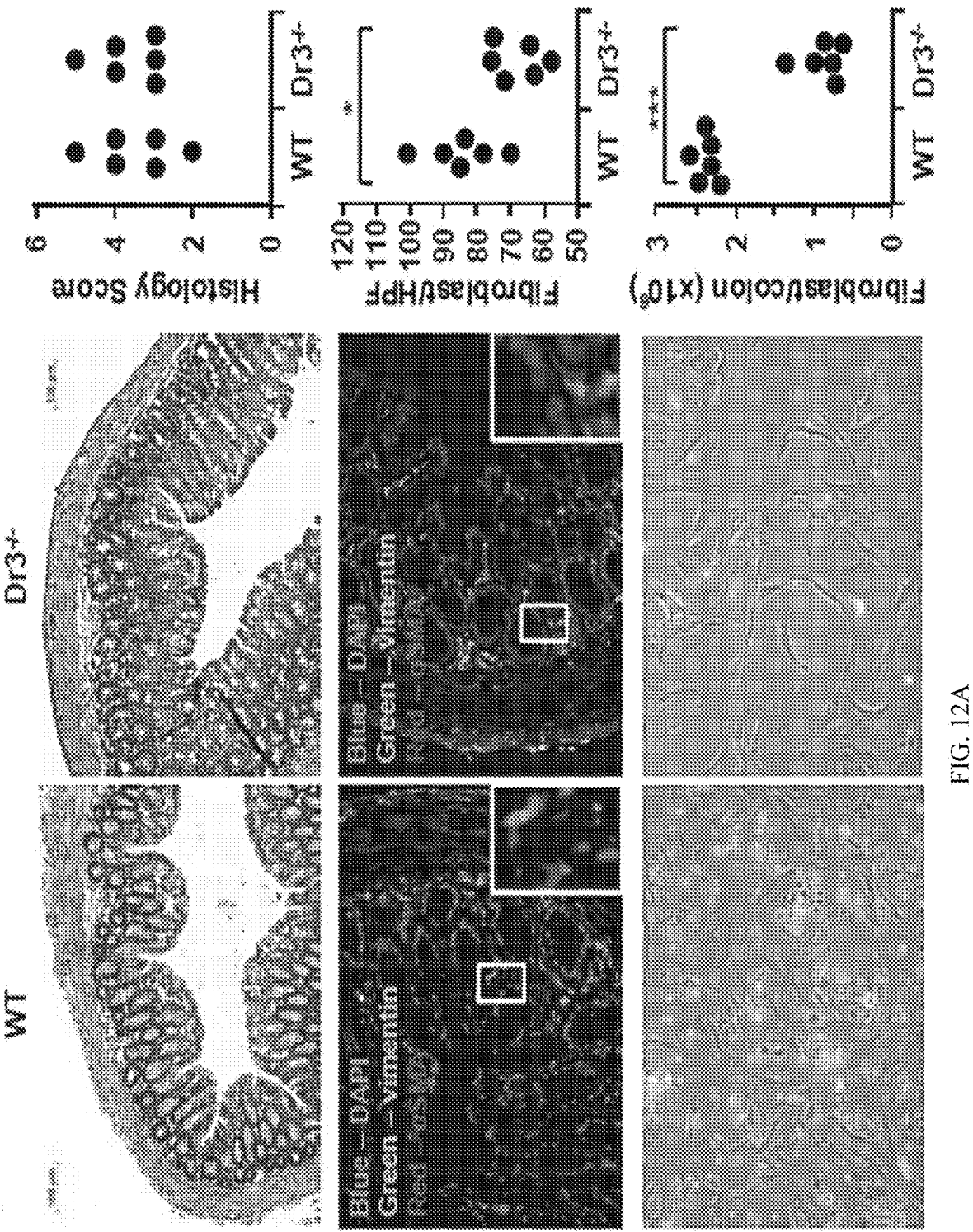
Figure 12B:
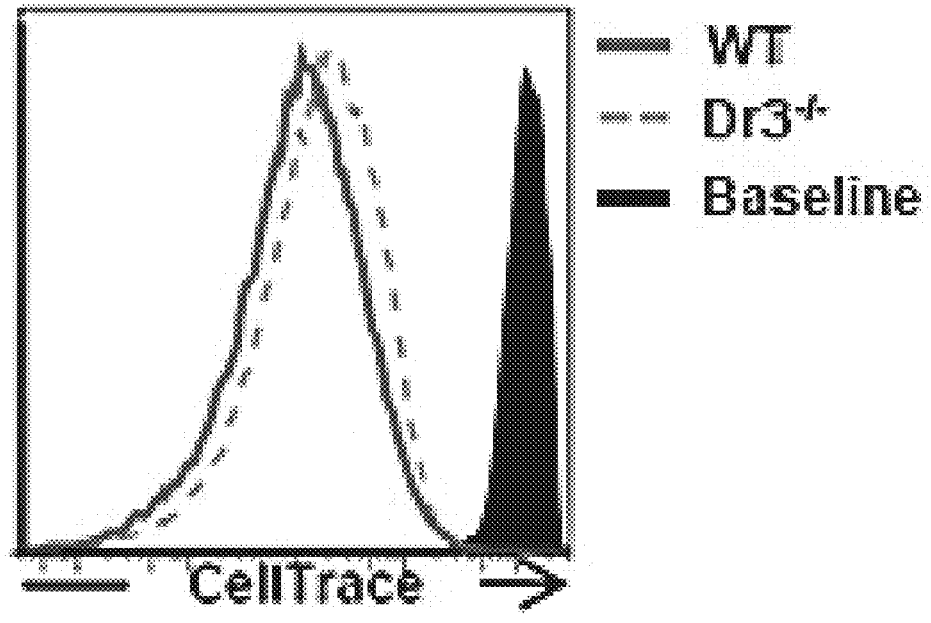
Figure 12C:
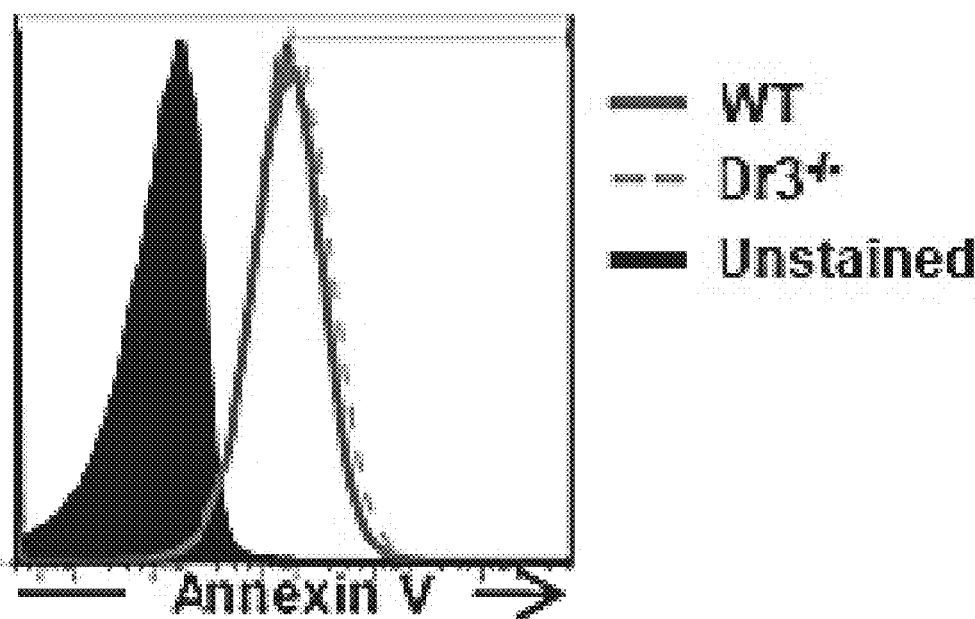

FIGS. 12A-12C depict, in accordance with an embodiment herein, reduced intestinal fibroblasts with DR3 deficiency.

FIG. 12A depicts representative H&E stained colon at 100× magnification with quantitation of inflammation on the upper panels. Representative Vimentin/αSMA stained colon at 200× magnification (insets are larger view at 200× magnification) with quantitation of fibroblasts per HPF is shown in the middle panels. Representative photographs of intestinal fibroblasts recovered from littermate WT and DR3−/− colon and individual total fibroblasts per colon are shown (bottom panels). Specifically, top panel shows there is no difference in histologic inflammation between wildtype and DR3KO colon to illustrate that it is not the underlying inflammation that is causing the reduced fibroblast number in DR3KO colon. Middle panel shows that there is reduced vimentin positive cells in DR3 deficient colon on direct staining in colon sections, this is important to show that the reduced fibroblast already pre-exist in the colon prior to fibroblast isolation from the colon. * $P<0.05$,  $P<0.01$, * $P<0.001$.

FIGS. 12B-12C depict representative flow cytometric histograms of proliferating fibroblasts and fibroblasts undergoing apoptosis, respectively, from WT and DR3−/− mice. Decreased CellTrace violet fluorescence intensity indicates proliferation. Increased Annexin V staining indicates apoptosis. Representative flow cytometric histograms of at least 6 independent experiments with similar results are shown.

Figure 13A:
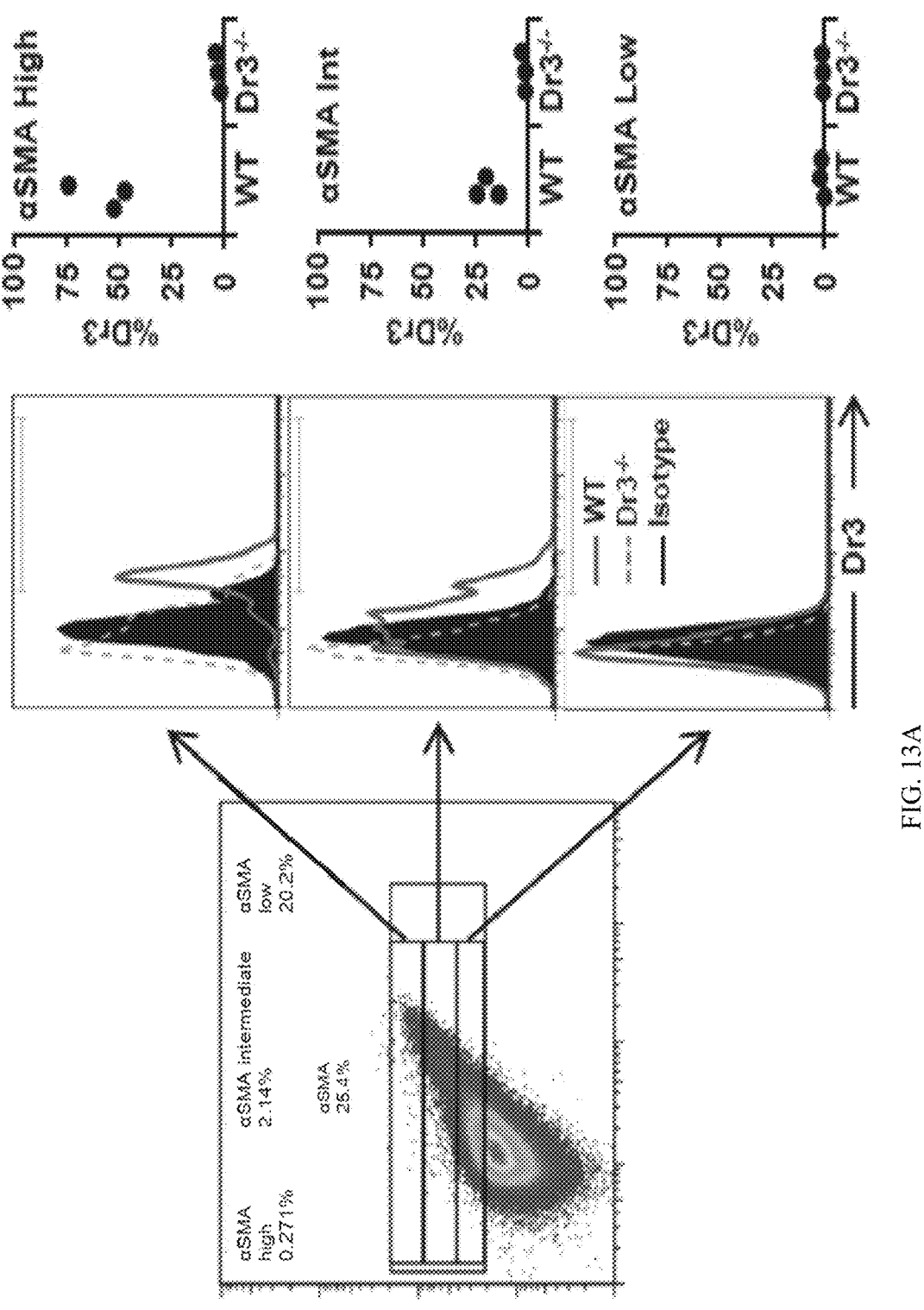
Figure 13B:
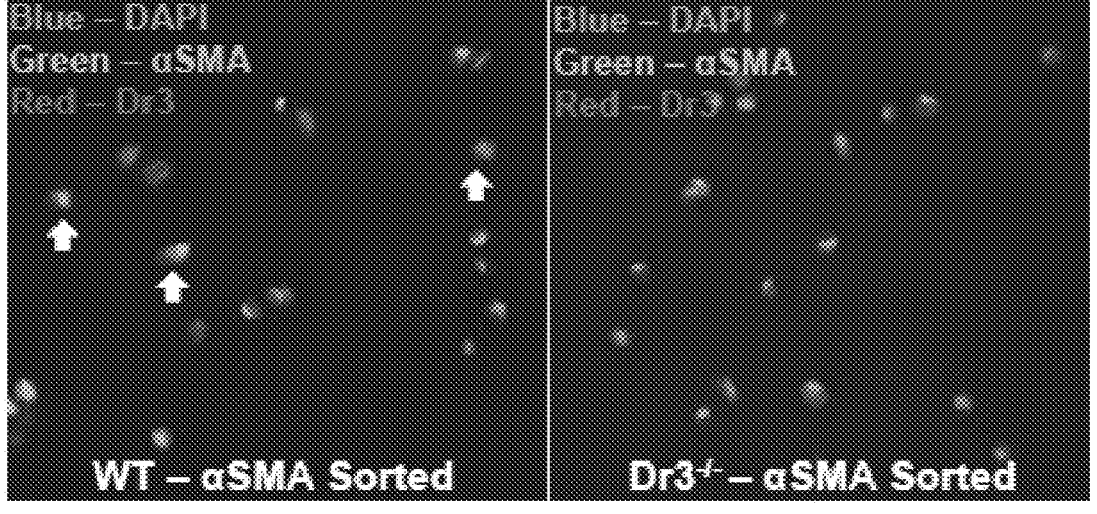
Figure 13C:
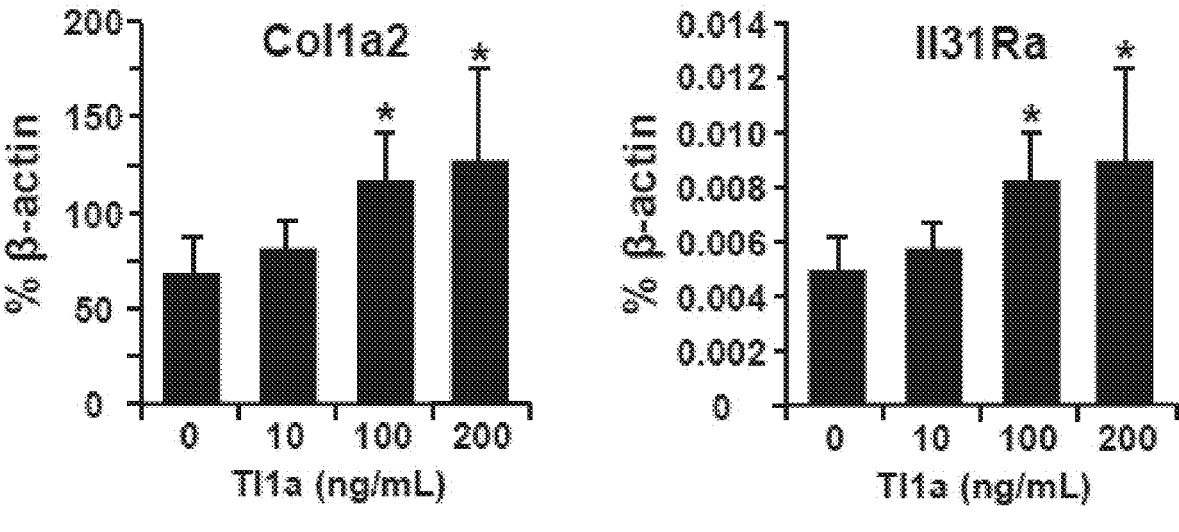

FIGS. 13A-13C depict, in accordance with an embodiment herein, intestinal fibroblasts express DR3 and respond to TL1A stimulation.

FIG. 13A depicts representative flow cytometric histograms of primary intestinal fibroblasts stained with DR3, αSMA and vimentin. Fibroblasts expressing high, intermediate, and low αSMA were gated as shown and DR3 staining is preferentially found in αSMA high>intermediate>low. Three independent experiments were performed. Specifically, FIG. 13A shows that there is a direct correlation between DR3 expression and alpha SMA expression. This is important to show that fibroblasts with higher alpha SMA expression (more active fibroblasts) has higher (DR3 expression), indicating that these more active fibroblasts are more receptive to TL1A signaling. For this experiment, the inventors have gated on the alpha SMA low, intermediate and high expressing myofibroblasts separately and then displayed the proportion of cells expressing DR3. The figure illustrates that DR3 is expressed in αSMA high>αSMA intermediate>αSMA low fibroblasts.

FIG. 13B depicts representative images of 3 independent sorted αSMA positive myofibroblasts at 200× magnification. There was co-staining of DR3 in WT, but not in DR3 deficient αSMA positive myofibroblasts. Specifically, FIG. 13B shows directly that DR3, the receptor for TL1A, is expressed on myofibroblasts. This is important to show that myofibroblasts which mediates fibrosis can receive signaling from TL1A. To do this experiment, the inventors sorted for αSMA positive cells that were stained with anti-alpha SMA and DR3 antibody. They then showed that DR3 is expressed on αSMA positive WT but not DR3 KO myofibroblasts using immunofluorescence microscopy.

FIG. 13C depicts the expression of Col1a2 and IL31Ra mRNA in WT primary intestinal fibroblasts with increasing TL1A stimulation (0-200 ng/mL), represented as mean±SD are shown (n=3). * $P<0.05$, ** $P<0.01$.

Figure 13D:
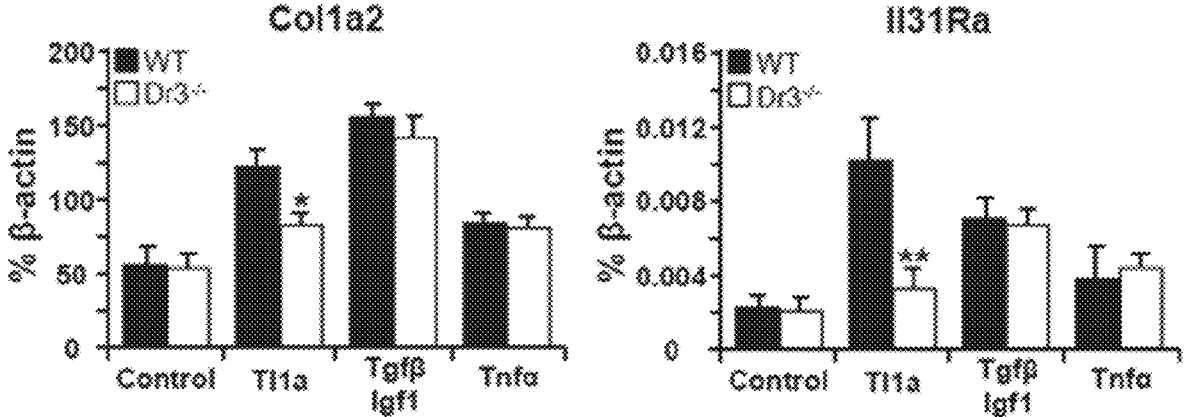

FIG. 13D depicts the induction of Col1a2 and IL31Ra mRNA by TL1A, Tgfβ/Igf1, and Tnfα in WT and DR3−/− intestinal represented as mean±SD (n=3). * $P<0.05$,  $P<0.01$. Specifically, FIG. 13D** shows additional experiments to enhance the in vitro experiments. The inventors used Tgfβ and Igf1 as prototypical fibroblast growth factors and showed that there is no difference in the induction of Col1a2 and IL31Ra expression between WT and DR3 deficient primary intestinal fibroblasts. They used Tnfα as the prototypical proinflammatory stimuli and showed that there is no difference in the induction of Col1a2 and IL31Ra comparing WT and DR3 deficient primary intestinal fibroblasts. This is in contrast to stimulation with TL1A where there is significant induction of Col1a2 and IL31Ra expression in the WT as compared to DR3 deficient primary intestinal fibroblasts.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 4th ed., J. Wiley & Sons (New York, NY 2012); March, Advanced Organic Chemistry Reactions, Mechanisms and Structure 5th ed., J. Wiley & Sons (New York, NY 2001); and Sambrook and Russel, Molecular Cloning: A Laboratory Manual 4th ed., Cold Spring Harbor Laboratory Press (Cold Spring Harbor, NY 2012); provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, intestinal fibrostenosis is among the hallmarks of severe Crohn's disease. Patients with certain TNFSF15 variants over-express TL1A and have a higher risk of developing strictures in the small intestine. Additionally, mice with sustained TL1A expression led to small and large intestinal fibrostenosis under colitogenic conditions. The inventors investigated whether neutralizing TL1A function can reverse established murine colitis and colonic fibrosis.

As further disclosed herein, TL1A blocking antibody (12F6A) or isotype control Ig was administered to mice with established chronic murine colitis and colonic fibrosis. Mice with DR3 deficiency (DR3−/−) were generated. Primary murine intestinal fibroblasts were isolated. Histological and immunofluorescent staining, flow cytometry, ELISA, and mRNA level were used to compare the degree of inflammation and fibrosis. CellTrace and Annexin V stains were used to determine cell proliferation and apoptosis, respectively. The inventors found that treatment with TL1A antibody mitigated murine colitis and reversed colonic fibrosis back to the original pre-inflamed levels. This could be due to lowered Ifnγ, IL17, Ctgf, IL31Ra expression and down-regulation of Tgfβ1 and Igf1 signaling. Additionally, blocking TL1A function led to reduced number of fibroblast and myofibroblast. Primary intestinal myofibroblasts express DR3 and can functionally respond to direct TL1A signaling by increasing collagen and IL31Ra expression. In conclusion, modulation of TL1A signaling inhibits both gut inflammation and fibrosis.

In one embodiment, the present invention provides a method of treating a disease in a subject, comprising providing a composition comprising an inhibitor of IL31 signaling, and administering an effective dosage of the composition to the subject. In another embodiment, the disease is a TL1A associated disease. In another embodiment, the disease is Inflammatory Bowel Disease (IBD). In another embodiment, the disease is associated with strictures developed in the small intestine and/or gut inflammation. In another embodiment, the disease is small and large intestinal fibrostenosis. In another embodiment, the disease is fibrosis. In another embodiment, the composition comprises one or more TL1A antibody. In another embodiment, the composition comprises one or more inhibitors of IL31Ra, IFNgamma, IL17, Ctgf, Tgfβ1 and/or Igf1 signaling.

In another embodiment, the present invention provides a method of treating a disease in a subject, comprising providing a composition comprising an inhibitor of IL31Ra signaling, and administering an effective dosage of the composition to the subject. In another embodiment, the disease is a TL1A associated disease. In another embodiment, the disease is Inflammatory Bowel Disease (IBD). In another embodiment, the disease is associated with strictures developed in the small intestine and/or gut inflammation. In another embodiment, the disease is small and large intestinal fibrostenosis. In another embodiment, the disease is fibrosis. In another embodiment, the composition comprises one or more TL1A antibody. In another embodiment, the composition comprises one or more inhibitors of IL31Ra, IFNgamma, IL17, Ctgf, Tgfβ1 and/or Igf1 signaling. In another embodiment, administering a therapeutically effective dosage of the composition decreases the number of fibroblasts and/or myofibroblasts in the subject.

In one embodiment, the present invention provides a method of diagnosing susceptibility to a TL1A associated disease in a subject, comprising obtaining a sample from the subject, assaying the sample to determine the presence or absence of a high level of IL31 expression relative to a normal individual, and diagnosing susceptibility to the TL1A associated disease based on the presence of the high level of IL31 expression relative to a normal individual. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises determining the presence of a high level of expression relative to a normal individual of IL31Ra, IFNgamma, IL17, Ctgf, Tgfβ1 and/or Igf1.

A method of diagnosing susceptibility to a TL1A associated disease in a subject, comprising obtaining a sample from the subject, assaying the sample to determine the presence or absence of a high level of IL31Ra expression relative to a normal individual, and diagnosing susceptibility to the TL1A associated disease based on the presence of the high level of IL31Ra expression relative to a normal individual. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the present invention further comprises determining the presence of a high level of expression relative to a normal individual of collagen, IL31Ra, IFNgamma, IL17, Ctgf, Tgfβ1 and/or Igf1.

In another embodiment, the present invention provides a method of diagnosing a TL1A associated disease in a subject, comprising obtaining a sample from the subject, assaying the sample to determine the presence or absence of one or more risk variants and/or markers associated with the TL1A associated disease, and diagnosing the TL1A associated disease based on the presence of one or more risk variants and/or markers associated with the TL1A associated disease. In another embodiment, the one or more risk variants and/or markers include a high expression of IL31Ra. In another embodiment, the one or more risk variants and/or markers include a high expression of IFNgamma, IL17, Ctgf, Tgfβ1 and/or Igf1. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises treating the TL1A associated disease by administering one or more TL1A inhibitors. In another embodiment, the method further comprises treating the TL1A associated disease by administering a TL1A inhibitor. In another embodiment, the subject is human. In another embodiment, the method further comprises treating the TL1A associated disease by administering a DR3 inhibitor.

As disclosed herein, in two distinct chronic colitis models, it was shown that TL1A Ab ameliorated colitic disease and reversed intestinal fibrosis. Modulation of TL1A signaling can alter the natural history of Crohn's disease by treating both gut inflammation and fibrosis. Blocking the TL1A/DR3 signaling pathway provides a therapeutic approach for the treatment of Crohn's disease and its associated complications including reversal of established fibrosis.

In one embodiment, the present invention provides a method of treating fibrosis associated with inflammatory bowel disease (IBD) in a subject by diagnosing fibrosis in the subject, and then administering one or more inhibitor of TL1A-DR3 signaling function, such as by administering a therapeutically effective TL1A antibody, or deleting DR3 expression, or dsRNA or siRNA coding for TL1A expression (expression of TNFSF15). Or, in other embodiments, by inhibiting one or more molecules downstream of TL1A-DR3.

In one embodiment, the present invention provides a method of treating a disease by administering a composition comprising a therapeutically effective dosage of TL1A inhibitor and/or DR3 inhibitor to the subject. In another embodiment, the disease is fibrosis. In another embodiment, the disease is inflammatory bowel disease. In another embodiment, the disease is Crohn's disease. In another embodiment, the disease is colitis. In another embodiment, the subject is a human. In another embodiment, the TL1A inhibitor is a TL1A antibody. In another embodiment, the DR3 inhibitor is a DR3 antibody.

In another embodiment, the present invention provides a method of reversing fibrosis in an individual by administering a composition comprising a therapeutically effective dosage of TL1A inhibitor and/or DR3 inhibitor to the subject.

In another embodiment, the present invention provides a method of treating fibrosis in a subject, comprising providing a composition comprising one or more inhibitors of TL1A-DR3 signaling function, and administering a therapeutically effective dosage of the composition to the subject. In another embodiment, the composition comprises one or more TL1A blocking antibodies. In another embodiment, the composition comprises one or more DR3 blocking antibodies. In another embodiment, the composition comprises one or more compounds that inhibit TL1A function by directly binding to TL1A. In another embodiment, the composition comprises one or more inhibitors of Ifngamma, IL17, Ctgf and IL31Ra. In another embodiment, the composition comprises one or more inhibitors of Tgfbeta1 and Igf1. In another embodiment, the composition comprises one or more inhibitors of IL31 signaling. In another embodiment, administering a therapeutically effective dosage of the composition results in reversal of the fibrosis to pre-inflamed levels. In another embodiment, the fibrosis is colonic fibrosis. In another embodiment, administering a therapeutically effective dosage of the composition further results in inhibition of gut inflammation in the subject. In another embodiment, administering a therapeutically effective dosage of the composition decreases the number of fibroblasts and/or myofibroblasts in the subject. In another embodiment, administering a therapeutically effective dosage of the composition decreases the number of primary intestinal myofibroblasts in the subject.

In one embodiment, the present invention provides a method of treating fibrosis in a subject, comprising providing a composition comprising a TL1A inhibitor and a DR3 inhibitor, and administering a therapeutically effective dosage of the composition to the subject. In another embodiment, the TL1A inhibitor is a TL1A antibody. In another embodiment, the DR3 inhibitor deletes expression of DR3. In another embodiment, the fibrosis is decreased. In another embodiment, the composition inhibits TL1A-DR3 signaling function.

In one embodiment, the present invention provides a method of reversing fibrosis in a subject, comprising providing a composition comprising a TL1A inhibitor and a DR3 inhibitor, and administering a therapeutically effective dosage of the composition to the subject. In another embodiment, the composition further comprises an inhibitor of IFNgamma, IL17, Tgfbeta1, Ctgf and/or IL31Ra signaling function. In another embodiment, the composition inhibits TL1A-DR3 signaling function.

In one embodiment, the present invention provides a method of treating inflammation, comprising providing a composition comprising a TL1A inhibitor and/or DR3 inhibitor, and administering a therapeutically effective dosage of the composition to the subject. In another embodiment, the composition further comprises an inhibitor of IFNgamma, IL17, Ctgf and/or IL31Ra signaling function. In another embodiment, the composition inhibits TL1A-DR3 signaling function.

In one embodiment, the present invention provides a method of treating a disease in a subject, comprising inhibiting Ifnγ and IL-17 expression, down-regulating Tgfβ signaling, and/or reducing fibroblast/myofibroblast, and treating the subject. In another embodiment, the disease is inflammatory bowel disease. In another embodiment, the disease is fibrosis. In another embodiment, the disease gut inflammation. In another embodiment, the disease is complications associated with inflammatory bowel disease.

In one embodiment, the present invention provides a method of treating complications associated with IBD, comprising providing a composition comprising an inhibitor of TL1A, DR3 and IL31Ra signaling function, and administering a therapeutically effective dosage of the composition to the subject. In another embodiment, the composition is administered intravenously to the subject.

In one embodiment, the present invention provides a composition comprising one or more TL1A inhibitors and/or one or more DR3 inhibitors, and a pharmaceutically acceptable carrier. In another embodiment, the one or more TL1A inhibitors are TL1A antibodies. In another embodiment, the one or more DR3 inhibitors are DR3 antibodies.

In another embodiment, the present invention provides a method of lowering inflammation in a subject by administering a composition comprising a therapeutically effective dosage of TL1A inhibitor and/or DR3 inhibitor to the subject.

In another embodiment, the present invention provides a method of inhibiting conditions associated with fibrosis by inhibiting Ifnγ and IL-17 expression, down-regulation of Tgfβ signaling, and/or reducing fibroblast/myofibroblast.

In one embodiment the present invention provides a composition comprising one or more inhibitors of TL1A, DR3 and IL31Ra signaling function, and a pharmaceutically acceptable carrier. In another embodiment, the one or more TL1A inhibitors is a TL1A antibody. In another embodiment, the one or more DR3 inhibitors is a DR3 antibody.

There are many techniques readily available in the field for detecting the presence or absence of polypeptides or other markers/biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The various methods and techniques described above provide a number of ways to carry out the invention. Of course, itis to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Induction of Chronic Colitis and Treatment

C57BL/6J mice were purchased from the Jackson Laboratory. Chronic dextran sodium sulfate (DSS) colitis was induced as described. 10 In the adoptive-transfer model, colitis was induced by intraperitoneal injection of 500,000 CD4+CD45RBhi naïve T-cells isolated from WT mice to Rag1−/− mice. Hamster anti-mouse TL1A Ab (12F6A, TEVA, North Wales, Pennsylvania) blocked the function of TL1A and were administered at 20-, or 80-mg/kg or control immunoglobulin (Ig) G (Leinco Technologies, St. Louis, Missouri) at 80-mg/kg dose were injected intraperitoneally into mice twice per week beginning on day 15 for the chronic DSS and day 29 for the adoptive-transfer models (FIG. 1A). Baseline controls (Rag Co or WT Co) were mice analyzed prior to DSS treatment or adoptive transfer of naïve T-cells. Pre-treatment (Pre-Tx) controls were mice analyzed at day 14 for the chronic DSS model and day 28 for the adoptive-transfer model. Treatment groups were mice analyzed at day 28 for the chronic DSS model and day 56 for the adoptive transfer model (FIG. 1A). All mice were maintained under specific pathogen-free conditions in the Animal Facility at Cedars-Sinai Medical Center (CSMC). This study was carried out in strict accordance with the Guide for the Care and Use of Laboratory Animals of the National Institutes of Health. Animal studies were approved by the CSMC Animal Care and Use Committee (protocol 3813).

Example 2

Disease Activity Index, Myeloperoxidase, Macroscopic and Histopathological Analyses Disease activity index (DAI) score was determined every other day for the DSS model and twice a week for the adoptive-transfer model as described. Myeloperoxidaseactivity was assessed using the Myeloperoxidase Fluorometric Detecton Kit according to the manufacturer's protocol (Enzo Life Sciences, Plymouth Meeting, PA). Macroscopic evidence of inflammation was scored blinded using the established classification. Tissue samples were processed and stained with hematoxylin and eosin (H&E) by the CSMC Histology-Core. Sirius red staining was performed using the NovaUltra Sirius Red Stain Kit according to manufacturer's protocol (IHC World, Woodstock, MD). Immunofluorescent stain was performed on 4 μM frozen sections fixed with 10% formalin and stained with α-SMA Ab (Abcam) at 1:100 dilution and α-Vimentin Ab (Covance, San Diego, CA) at 1:2000 dilution with donkey α-rabbit IgG and goat α-chicken IgY (Abcam, Cambridge, MA) secondary Ab. Histopathological scores were assigned in a blinded manner by two trained animal pathologists (DQS and JC) as described. Observation of ≥5 different fields per gut region per mouse was used to determine histologic score and collagen deposition at 200× magnification and to count fibroblast/myofibroblast numbers at 630× magnification using a Leica TCS SP spectral confocal microscope.

Example 3

Generation of DR3−/− Mice

Cloning of DR3 targeting vector and generation of DR3+/− founder mice were performed in collaboration with genOway (genOway, Lyon, France). Briefly, DR3 endogenous locus containing 1.5 kb upstream of exon 1 and 3 kb downstream of exon 8 were generated by PCR amplification using genomic DNA from C57BL/6J mice and cloned into the pCR4-TOPO vector (Invitrogen, Carlsbad, CA). Subsequently, two loxP sites were inserted flanking DR3 exons 2 to 5 (FIG. 5A). Positive selection neomycin gene flanked by FRT sites was inserted to the intron between exon 1 and 2 to generate the targeting vector (FIG. 5A). Every step of the cloning process was validated through restriction analysis and sequencing. The DR3 gene targeting construct was linearized and transfected into genOway proprietary embryonic stem (ES) cells with C57BL/6J background by electroporation. Homologous recombinants were selected by G418 and confirmed by Southern blot analysis. ES clones with correct 5' and 3' recombination were microinjected into C57BL/6J blastocysts and introduced into pseudopregnant C57BL/6J mice. Male chimeric offspring were bred to obtain germ line mutant mice which were then bred to Flpe delete mouse strain to remove the neomycin cassette, then bred to Cre delete mice to excise the loxP flanked sequences (FIG. 5A), confirmed by Southern blot, and maintained on the C57BL/6J genetic background.

Example 4

Expression Analysis

Total RNA was isolated using RNEASY™ Microarray Tissue Mini Kit (QIAGEN™, Valencia, CA), and reverse-transcription polymerase chain reaction (RT-PCR) was performed using RT2 HT First Strand and gene expression was measured using the RT2 Custom Fibrosis Array CAPM11248 (QIAGEN™, Valencia, CA) kits per manufacturer's protocols. Cytokine concentration was assayed using a multi-plex immunoassay, Mouse Th1/Th2/Th17/Th22 13plex Kit FlowCytomix (EBIOSCIENCE™, San Diego, CA) per manufacturer's protocol. Validated Dr3 qPCR assay Mm.PT.51.17321439, I131Ra qPCR assay Mm.PT.56a.32787326 and β-actin qPCR assay Mm.PT.39a.22214843 were purchased from IDT Technologies (Skokie, IL).

US 12,590,160 B2

17

Example 5

Cell Isolation, Culture, Intracellular Cytokine
Expression, and Flow Cytometry

Isolation and culture of lamina propria mononuclear cells
(LPMC), mesenteric lymph node (MLN), and splenic cells
and their subsequent stimulation by anti-CD28 and anti-
CD38 were carried out. The inventors used the whole colon
and the distal 10 cm of the ileum for LPMC isolation. Mouse
primary colonic fibroblasts were isolated from colon that
were incubated in 1 mM DTT (Fisher ScientificFISHER
SCIENTIFIC™, Tustin, CA), 37° C., 15 min, and then 1
mM DTT with 5 mM EDTA (PromegaPROMEGA™, Madi-
son, WI), 37° C., 30 min. The remaining colonic tissues were
rinsed by 1×HBSS (Corning Cellgro, Swedesboro, NJ),
minced and then digested for 30 min at 37° C. with 1.5
mg/mL Collagenase II (Worthington, Lakewood, NJ), 0.3
mg/mL DNase I and 3 mg/mL Hyaluronidase (Sigma, St.
Louis, MO) in DMEM (Corning Cellgro, Swedesboro, NJ).
The isolated cells were cultured in DMEM supplemented
with 10% FCS, Penicillin/Streptomycin (100 IU/mL), and
Fungizone (0.5 μg/mL). Primary intestinal fibroblasts were
used at passage 2. Cells were acquired on a LSR II flow-
cytometer (BD Biosciences, San Jose, CA) and analyzed
using FlowJeFLOWJO™ analysis software.

Example 6

Ex Vivo Intestinal Fibroblast Proliferation and
Apoptosis Assay

Primary intestinal fibroblasts were isolated and stained
with CellTrace Violet (INVITROGEN™, Carlsbad, CA) per
manufacturer's instructions. Stained cells were then incu-
bated with 100 ng/mL of TL1A in DMEM supplemented
with 10% FCS, Penicillin/Streptomycin (100 IU/mL), and
Fungizone (0.5 μg/mL). After 48 hours, cultured intestinal
fibroblasts were stained using Annexin V Apoptosis Detec-
tion Kit (EBIOSCIENCE™, San Diego, CA) per manufac-
turer's instructions. After Annexin V stain, fibroblasts were
harvested, washed and fixed with 2% paraformaldehyde and
subjected to flow cytometric analysis with BD LSR II
flow-cytometer and analyzed by FLOWJO™ software.

Example 7

Statistical Analysis

Data are presented as the mean±standard deviation (SD).
Comparison between two groups was performed by a two-
tailed Fisher's Exact Test for categorical variables and
Student's t-test for continuous variables. Parametric and
non-parametric tests were used depending on the fulfillment
of the test assumptions. Comparison between three groups
was done using ANOVA, followed by pair wise post-hoc
analysis with Turkey's HSD and Behrens-fisher-Test cor-
rection for the multiple comparisons. p<0.05 was considered
significant.

Example 8

TL1A Ab Administration Attenuated Disease
Activity and Gross Inflammation of Established
Chronic Colitis The effect of neutralizing TL1A function in chronic
murine colitis was evaluated using TL1A Ab in immune-deficient Rag1−/− mice that were adoptively transferred
with naïve CD4+CD45RBhi T-cells. TL1A Ab at 20-, and
80-mg/kg or isotype control Ab (Iso Ab) at 80-mg/kg was
administered two times per week beginning on day 29 post
transfer when colitis was established (FIG. 1A). By week 6
and continuing through the end of the study at week 8, the
disease activity index (DAI) of mice treated with TL1A Ab
was significantly lower than mice receiving the Iso Ab (FIG.
1B). Compared to the Iso Ab group, gross colonic inflam-
mation was significantly reduced in mice that received
TL1A Ab at both doses (FIG. 1C). The number of mono-
nuclear cells recovered from mesenteric lymph nodes
(MLN) and the lamina propria (LP) was also reduced with
TL1A Ab treatment as compared to the iso Ab group (FIG.
1D). In the TL1A 80-mg/kg Ab treated mice, amelioration of
established colitis and cellular infiltrates was demonstrated
by less severe gross colonic inflammation and significantly
reduced numbers of LP mononuclear cells (LPMC) than the
Pre-Tx group (FIGS. 1C-1D).

Similar findings were obtained using the chronic DSS
colitis model. In this model, TL1A Ab (20-mg/kg) was
administered twice a week beginning at day 15 when colitis
was established (FIG. 1A). Compared to the Iso Ab group,
we observed lower DAI (FIG. 7A), reduced gross inflam-
mation (FIG. 7B), and fewer recovered mononuclear cells
from MLN and LP (FIG. 7C). The reduction of DAI and
mononuclear cells was also less than the Pre-Tx group.
These data showed that treatment with TL1A Ab resulted in
decreased gross indicators of inflammation and reduced
accumulation of inflammatory cells in the intestine.

Example 9

TL1A Ab Administration Mitigated Histopathologic
Features of Established Murine Colitis Histologic examination of the colon revealed reduced
inflammation characterized by reduced cellular infiltrate,
mucin depletion, crypt abscess, and architectural changes
with TL1A Ab therapy compared to Iso Ab group in the
adoptive transfer model (FIGS. 2A-2B). The reduction in
histological inflammation was also significantly reduced
compared to the 4 week Pre-Tx group (FIGS. 2A-2B),
indicating partially resolved inflammation. Consistently,
colonic myeloperoxidase (MPO) activity was significantly
reduced with both doses of TL1A Ab administration as
compared to the Iso Ab group and with 80-mg/kg of TL1A
Ab as compared to the Pre-Tx group (FIG. 2C). Mucosal
resolution of colitis was suggested when the reduction in
colonic MPO activity with TL1A Ab dose reached a level
not significantly different than the Rag baseline control (Rag
Co) group (FIG. 2C).

Similarly, there was improved colon histopathology with
TL1A Ab as compared to both the Iso Ab and Pre-Tx group
in the chronic DSS model (FIGS. 8A-8B). Although there
were reduction in histologic inflammation with TL1A Ab
treatment, colonic inflammation is still significantly higher
as compared to baseline WT Co group (FIG. 8B). In
addition, colonic MPO activity was significantly lower with
TL1A Ab treatment as compared to both the Iso Ab and the
Pre-Tx group (FIG. 8C). These results showed that admin-
istration of TL1A Ab resulted in normalization of colonic
histopathology.

Example 10

TL1A Ab Inhibited Th-1 and -17 Immune
Responses

To assess the potential immune mechanisms of reduced
established murine colitis in the two colitogenic models, the expression of Ifnγ, IL13, and IL17 was measured. TL1A Ab reduced the frequency of CD4+IL17+ T-cells in MLN and LPMC compared to both the Iso Ab group and Pre-Tx group in the adoptive transfer model (FIGS. 3A-3B). CD4+Ifnγ+ T-cells were similarly reduced with both doses of TL1A Ab treatment except in LPMC where TL1A Ab at 20-mg/kg did not result in a significant reduction as compared to the Pre-Tx group (FIGS. 3A and 3C). Additionally, the inventors also found significantly reduced Ifnγ+ and IL17+ double positive CD4+ T-cells with TL1A Ab treatment as compared to Pre-Tx and Iso Ab groups in both MLN and LPMC (FIGS. 3B and 3C, right panel). Using MLN and LPMC cells that were stimulated with CD3/CD28, lower IL17 production was seen in mice treated with TL1A Ab as compared to mice that received Iso Ab and the pre-treatment group (FIG. 3D). Except in the MLN, TL1A Ab treatment at both doses led to lower Ifnγ secretion as compared to Iso Ab and the Pre-Tx group (FIG. 3E). The percentage of CD4+IL13+ T-cells and IL13 production was not significantly different among the groups. In the chronic DSS colitis model, reduction of CD4+IL17+, CD4+Ifnγ+ and CD4+IL17+Ifnγ+ T-cells was similarly observed in MLN and LPMC with TL1A Ab treatment (FIGS. 9A-9C). Consistently, TL1A Ab treatment resulted in lower production of IL17 and Ifnγ in isolated MLN and LPMC cells that were stimulated with CD3/CD28 (FIGS. 9D-9E). The percentages of CD4+IL13+ T-cells and IL13 production were not different among the groups in the chronic DSS colitis model. These data suggested that TL1A Ab reduced Th-1 and -17 proinflammatory immune responses.

Example 11

TL1A Ab Reversed Established Colonic Fibrosis

Mice with constitutive TL1A expression were previously shown to develop increased gut fibrosis. To assess whether blocking TL1A signaling can reduce colonic fibrosis, we performed Sirius red stain to measure the degree of collagen deposition. The inventors found increased collagen deposition by the 4th week after naïve T cell transfer in the Pre-Tx group compared to baseline Rag Co group (FIGS. 4A and 4C). The degree of collagen deposition became greater by the 8th week in mice receiving control Iso Ab. However, treatment with TL1A Ab led to significant reduction in collagen deposition when compared to mice that received the Iso Ab or the Pre-Tx group (FIGS. 4A and 4C). Notably, collagen deposition was not significantly different when 80 mg/kg of TL1A treatment was compared to normal Rag Co mice (FIG. 4C). In the chronic DSS model, similar reduction in collagen deposition with TL1A Ab treatment as compared to Iso Ab or the Pre-Tx group was observed (FIGS. 4A and 4C). In addition, TL1A treatment led to a reduction in collagen deposition to a level that was not statistically different than WT baseline control (FIGS. 4A and 4C). Together, these data suggested that blocking TL1A signaling reversed collagen deposition to similar levels prior to the onset of inflammation.

Example 12

Blocking TL1A-DR3 Signaling Reduced Intestinal Fibroblast and Myofibroblast Number To begin to study the mechanism of collagen deposition reduction with TL1A Ab, the frequency of intestinal fibroblasts and myofibroblasts was measured. Intestinal myofibroblasts are a cell population involved in gut fibrogenesis. Vimentin positive cells are fibroblasts, which in the context of co-expression of alpha smooth muscle actin (αSMA), represent myofibroblasts. The data showed that 4 weeks after naïve T-cell transfer (Pre-Tx group), the number of fibroblasts and myofibroblasts increased (FIGS. 4B and 4D). The number of fibroblasts and myofibroblasts further increased by 8th week in mice receiving Iso Ab. However, treatment with TL1A Ab led to a reduction in the number of fibroblasts and myofibroblasts to levels similar to normal Rag Co (FIGS. 4B and 4D). Interestingly, the reduction in myofibroblasts in the mice that received 80-mg/kg of TL1A Ab reached a level that was not statistically different than Rag Co mice (FIGS. 4B and 4D), suggesting reversal of fibrogenesis.

In the chronic DSS model, similar reduction in the number of fibroblasts and myofibroblasts with Ab treatment when compared to isotype or the Pre-Tx group was observed (FIGS. 4B and 4D). Consistent with the adoptive transfer model, the reduction in the number of gut fibroblasts and myofibroblasts with TL1A Ab treatment reached a level that was not statistically different from WT baseline control (FIGS. 10B and 10D).

The inventors generated DR3 deficient (DR3−/−) mice (FIGS. 5A and 5B) to delineate whether the reduction in the number of intestinal fibroblasts and myofibroblasts is due to direct TL1A-DR3 signaling. There were significantly fewer intestinal fibroblasts in DR3−/− as compared to wildtype littermate baseline (non-colitic) mice (FIG. 5C). Next, the inventors performed ex vivo CellTrace Violet assay and Annexin V stain to determine whether the difference in intestinal fibroblasts between WT and DR3−/− mice is due to proliferation and/or apoptosis, respectively. Flow cytometric analysis showed similar rates of proliferation as evident by the overlapping CellTrace Violet intensity between WT and DR3−/− intestinal fibroblasts (FIG. 5D, top panel). No differences were observed in the rate of apoptosis between wildtype and DR3−/− intestinal fibroblasts (FIG. 5D, bottom panel).

Example 13

Reversal of Fibrogenesis With TL1A Ab Therapy

To study the molecular mechanisms of reversal of established intestinal fibrosis with TL1A Ab, the expression of collagen, fibrogenic program mediators (Tgfβ1, Ctgf, Igf1, Pten, and IL31Ra), and factors (Mmp and Timp) involved in extracellular matrix (ECM) remodeling were measured. Lower levels of collagen expression were found in both the adoptive transfer and chronic DSS models (Table 1 and Table 2 herein). Normalization in the fibrogenic program with TL1A Ab was observed with lower expression of pro-fibrotic mediators including Tgfβ1 and IL31Ra in both the adoptive transfer and chronic DSS models and Igf1 in the adoptive transfer model (Table 1 and Table 2). The expression of connective tissue growth factor (Ctgf), a downstream mediator of Tgfβ signaling, was reduced with TL1A Ab administration as compared to Pre-Tx and Iso Ab groups in the adoptive transfer model. ECM remodeling was assessed by measuring the expression of metalloproteases (Mmp) and tissue inhibitors of metalloproteases (Timp). Compared to the isotype Ab group, the expression of genes involved in ECM degradation was reduced in mice treated with TL1A Ab in the adoptive transfer model (Mmp2, Mmp3; Table 1) and in the chronic DSS model (Mmp2, Mmp3, Mmp13; Table 2). Notably, the expression of Timp was lower with TL1A treatment in the adoptive transfer model (Timp2, Table 1) and in the chronic DSS model (Timp1, Timp2; Table 2). These results demonstrate that there is a reduction in the fibrogenic program with TL1A Ab, which leads to decreased collagen synthesis. The lower expression of both Mmp and Timp may contribute to the enhanced removal of established ECM components rather than inducing tissue damage. Thus, the data suggest that reversal of established fibrosis by TL1A Ab might be the net result of the reduced fibrogenic program and possibly the reduction of both Mmp and Timp.

Example 14

Intestinal Fibroblasts Express DR3 and Respond to TL1A Stimulation

The inventors investigated whether intestinal fibroblasts can functionally respond to direct TL1A signaling. mRNA levels of DR3, the only known receptor for TL1A, were measured and found to be expressed at low levels in WT but not in DR3 deficient primary intestinal fibroblasts (FIG. 6A, top panel). Consistently, immunofluorescent staining showed that DR3 is expressed on WT primary intestinal fibroblasts (FIG. 6A, bottom panel). Using flow cytometry, the inventors found that DR3 is expressed preferentially on fibroblasts that co-express αSMA as compared to fibroblasts without αSMA expression (FIG. 6B). The inventors next checked whether intestinal fibroblasts can respond to TL1A stimulation and used collagen (Col1a2) and IL31 receptor (IL31Ra) as markers of fibroblast activation. The inventors showed that TL1A can dose dependently increase the expression of Col1a2 and IL31Ra in murine primary intestinal fibroblasts ex vivo (FIG. 6C). The specificity of TL1A stimulation is demonstrated by the blunted TL1A induction of Col1a2 and IL31Ra in DR3−/− murine intestinal fibroblasts ex vivo (FIG. 6D). These data indicate that intestinal fibroblasts express DR3 and can functionally respond to direct TL1A signaling.

Example 15

Results for Expression Analysis of Fibrosis Mediators

TABLE 1

Expression analysis of fibrosis mediators in the adoptive transfer colitis model.

| | baseline | Pre-Tx | Iso Ab | Tl1a Ab - 80 mg/kg | | | |
|---|---|---|---|---|---|---|---|
| | | | | | | p vs. | |
| | % β-actin n = 6 | % β-actin n = 6 | % β-actin n = 7 | % β-actin n = 6 | Rag | Pre-Tx | Iso Ab |
| col1a1 | 0.19 ± 0.12 | 0.19 ± 0.12 | 0.21 ± 0.10 | 0.11 ± 0.03 | ns | 0.024 | 0.03 |
| col1a2 | 0.49 ± 0.29 | 0.76 ± 0.32 | 1.23 ± 0.78 | 0.39 ± 0.12 | ns | 0.024 | 0.026 |
| col3a1 | 12.69 ± 3.61 | 16.45 ± 3.93 | 16.08 ± 4.04 | 9.66 ± 3.44 | ns | 0.0073 | 0.014 |
| col4a1 | 1.54 ± 0.32 | 1.95 ± 0.32 | 1.88 ± 0.84 | 1.19 ± 0.33 | ns | 0.00055 | ns |
| Tgfβ1 | 0.16 ± 0.06 | 0.40 ± 0.16 | 0.50 ± 0.17 | 0.25 ± 0.06 | 0.018 | 0.046 | 0.003 |
| Ctgf | 0.66 ± 0.13 | 1.04 ± 0.40 | 1.04 ± 0.32 | 0.54 ± 0.08 | ns | 0.021 | 0.007 |
| Igf1 | 0.32 ± 0.06 | 0.53 ± 0.18 | 0.73 ± 0.36 | 0.41 ± 0.15 | ns | ns | 0.047 |
| Pten | 3.80 ± 0.75 | 2.28 ± 0.53 | 1.86 ± 0.25 | 2.03 ± 0.67 | 0.0015 | ns | ns |
| Il31Ra | 0.003 ± 0.001 | 0.005 ± 0.002 | 0.007 ± 0.003 | 0.004 ± 0.001 | ns | ns | 0.034 |
| Mmp2 | 0.32 ± 0.072 | 0.43 ± 0.12 | 0.44 ± 0.13 | 0.28 ± 0.07 | ns | 0.015 | 0.015 |
| Mmp3 | 0.046 ± 0.022 | 1.15 ± 1.15 | 1.18 ± 0.70 | 0.34 ± 0.37 | 0.043 | ns | 0.036 |
| Mmp13 | 0.047 ± 0.015 | 0.20 ± 0.17 | 0.18 ± 0.08 | 0.10 ± 0.06 | ns | ns | ns |
| Timp1 | 0.038 ± 0.014 | 0.19 ± 0.24 | 0.18 ± 0.12 | 0.14 ± 0.07 | 0.016 | ns | ns |
| Timp2 | 1.11 ± 0.27 | 0.86 ± 0.15 | 0.79 ± 0.12 | 0.50 ± 0.18 | 0.001 | 0.001 | 0.048 | ns = not significant

TABLE 2

Expression analysis of fibrosis mediators in the DSS model.

| | WT | Pre-Tx Co | Isotype Co | Tl1a Ab - 20 mg/kg | | | |
|---|---|---|---|---|---|---|---|
| | | | | | | p vs. | |
| | % β-actin n = 6 | % β-actin n = 5 | % β-actin n = 5 | % β-actin n = 5 | WT | Pre-Tx | Isotype |
| col1a1 | 0.54 ± 0.45 | 0.55 ± 0.36 | 0.67 ± 0.45 | 0.30 ± 0.17 | ns | ns | ns |
| col1a2 | 0.67 ± 0.26 | 1.20 ± 0.94 | 1.19 ± 0.93 | 0.63 ± 0.31 | ns | ns | ns |
| col3a1 | 35.79 ± 10.95 | 38.64 ± 18.02 | 35.18 ± 9.74 | 23.28 ± 3.47 | 0.044 | ns | 0.036 |
| col4a1 | 2.60 ± 1.08 | 2.62 ± 1.37 | 2.70 ± 0.54 | 1.83 ± 0.10 | ns | ns | 0.010 |
| Tgfβ1 | 0.21 ± .06 | 0.38 ± 0.15 | 0.43 ± 0.03 | 0.22 ± 0.04 | ns | 0.041 | 6.943E−05 |
| Ctgf | 0.97 ± .27 | 1.1 ± .32 | 1.14 ± .36 | 0.84 ± .21 | ns | ns | ns |
| Igf1 | 0.48 ± 0.18 | 0.85 ± 0.63 | 1.09 ± 0.52 | 0.65 ± 0.28 | ns | ns | ns |
| Pten | 0.004 ± 0.003 | 0.008 ± 0.004 | 0.012 ± 0.003 | 0.008 ± 0.002 | ns | ns | ns |
| Il31Ra | 3.13 ± 0.65 | 2.58 ± 0.61 | 2.67 ± 0.97 | 2.69 ± 0.31 | 0.020 | ns | 0.046 |
| Mmp2 | 0.52 ± 0.16 | 0.60 ± 0.29 | 1.21 ± 0.38 | 0.52 ± 0.25 | ns | ns | 0.007 |
| Mmp3 | 0.03 ± 0.015 | 2.07 ± 3.70 | 1.91 ± 0.10 | 0.42 ± 0.27 | 0.003 | ns | 1.48E−05 |

TABLE 2-continued

| | | | | | | |
|---|---|---|---|---|---|---|
| | | Expression analysis of fibrosis mediators in the DSS model. | | | | |
| | WT | Pre-Tx Co | Isotype Co | Tl1a Ab - 20 mg/kg | | |
| | % β-actin | % β-actin | % β-actin | % β-actin | | p vs. |
| | n = 6 | n = 5 | n = 5 | n = 5 | WT | Pre-Tx | Isotype |
| Mmp13 | 0.05 ± 0.011 | 0.61 ± 1.07 | 1.02 ± 0.21 | 0.21 ± 0.15 | 0.014 | ns | 0.0003 |
| Timp1 | 0.04 ± 0.024 | 0.32 ± 0.37 | 0.33 ± 0.06 | 0.15 ± 0.07 | 0.003 | ns | 0.004 |
| Timp2 | 1.02 ± 0.32 | 0.88 ± 0.17 | 1.12 ± 0.11 | 0.74 ± 0.14 | ns | ns | 0.005 | ns = not significant

Example 16

Blocking TL1A-DR3 Signaling Reduced Numbers of Intestinal Fibroblasts and Myofibroblasts-Additional Results Colonic myofibroblasts are a cell population involved in gut fibrogenesis. To study the cellular mechanisms of collagen deposition reduction with TL1A Ab, fibroblast expression of vimentin and myofibroblast coexpression of vimentin and alpha smooth muscle actin (αSMA) were measured to assess the numbers of these cell types. After naïve T-cell transfer in both the Pre-Tx and Iso Ab groups, the numbers of colonic fibroblasts and myofibroblasts were increased (FIG. 11A). However, treatment with TL1A Ab led to a reduction in the number of fibroblasts and myofibroblasts to levels similar to normal Rag Co (FIG. 11A).

In the chronic DSS model, mice treated with TL1A Ab exhibited a similar reduction in the number of colonic fibroblasts and myofibroblasts compared to the Iso or the Pre-Tx groups (FIG. 11B). Consistent with what was observed in the adoptive transfer model, the number of gut fibroblasts and myofibroblasts with TL1A Ab treatment reduced to a level that was not statistically different from WT baseline control (FIG. 11B). Because there was still significantly worsened colitis with TL1A Ab treatment as compared to WT Co group in the chronic DSS colitis model, the reduced numbers of myofibroblasts and fibroblasts is consistent with at least in part, a direct consequence of neutralizing TL1A, rather than solely a secondary effect through reduced inflammation.

It was next assessed whether there were DR3 expression changes in association with fibrotic changes in these murine models of chronic colitis. Immunofluorescent staining revealed increased DR3 expression in the Pre-Tx and Iso Ab groups as compared to both baseline control groups (Rag Co and WT Co) and the TL1A Ab treated groups in both the adoptive transfer and chronic DSS colitis models (FIGS. 11C-11D). Notably, there was expression of DR3 in a percentage of fibroblasts in the Pre-Tx and Isotype Ab groups (FIGS. 11C-11D). Real-time quantitative reverse transcriptase-PCR analysis showed that the expression of DR3 was significantly higher in the Iso Ab group as compared to mice in the both baseline control (Rag Co and WT Co) and TL1A Ab treatment groups in both models (FIG. 11E). Additionally, TL1A mRNA expression was significantly increased in the Iso Ab group as compared to uninflamed controls (Rag Co and WT Co) and the TL1A Ab treatment groups in both the adoptive transfer and chronic DSS colitis models (FIG. 11F). These results are consistent with a direct relationship between DR3 TL1A expression and increase in intestinal fibrosis.

To determine whether the reduction in the number of intestinal fibroblasts and myofibroblasts could be due to direct TL1A-DR3 signaling, DR3 deficient (DR3-/-) mice were generated. Although there was no spontaneous colitis in either WT or DR3-/- mice up to 8 weeks of age (FIG. 12A, top panel), there were significantly fewer intestinal fibroblasts in DR3-/- as compared to WT littermate mice as shown by immunofluorescent staining of vimentin (FIG. 12A, middle panel) and quantitation of the total recovered fibroblasts per colon (FIG. 12a, bottom panel). There were no morphological differences between WT and DR3-/- fibroblasts by immunofluorescent staining with vimentin and αSMA (FIG. 12A, middle panel) or with light microscopy (FIG. 12A, bottom panel). Ex vivo CellTrace Violet assay and Annexin V stain were used to determine whether the difference in the numbers of intestinal fibroblasts between WT and DR3-/- mice was due to proliferation and/or apoptosis, respectively. Flow cytometric analysis showed similar rates of proliferation as evidenced by the overlapping CellTrace Violet intensity between WT and DR3-/- intestinal fibroblasts (FIG. 12B). No differences were observed in the rate of apoptosis between WT and DR3-/- intestinal fibroblasts (FIG. 12C).

Example 17

Intestinal Fibroblasts Express DR3 and Respond to TL1A Stimulation Additional Results To determine whether intestinal fibroblasts functionally respond to direct TL1A signaling mRNA levels of DR3 were measured and found to be expressed at low levels in WT (0.0018±0.001% β-actin) but undetectable in DR3 deficient primary intestinal fibroblasts. Flow cytometric analysis was performed to determine whether DR3 was expressed on vimentin+αSMA-fibroblasts or vimentin+αSMA+ myofibroblasts. The results showed that DR3 was expressed preferentially on vimentin+αSMA+ myofibroblasts as compared to vimentin+αSMA-fibroblasts. Additionally, there was a direct correlation of DR3 expression with αSMA levels on myofibroblasts; with a higher proportion of DR3 expression on myofibroblasts with the highest αSMA expression (FIG. 13A). Additionally, sorted αSMA positive primary intestinal fibroblasts that were immunostained with αSMA and DR3 showed co-staining of DR3 in WT but not in DR3 deficient myofibroblasts, indicating that DR3 was expressed on αSMA positive primary intestinal fibroblasts (FIG. 13B).

To determine whether intestinal fibroblasts could respond to direct TL1A stimulation, changes in the expression of collagen (Col1a2, marker for fibroblast function) and IL31Ra (IL31Ra is expressed on fibroblasts) were measured with the addition of exogenous TL1A protein. Results showed a TL1A dose-dependent increase in the expression of Col1a2 and IL31Ra in murine primary intestinal fibroblasts ex vivo (FIG. 13C). The specificity of TL1A stimulation was demonstrated by the blunted TL1A induction of Col1a2 and IL31Ra in DR3−/− murine intestinal fibroblasts ex vivo (FIG. 13D). In contrast, a differential induction of Col1a2 or IL31 Ra was not seen using known fibroblast growth factors (Tgfβ and Igf1) or proinflammatory stimuli (Tnfα) (FIG. 13D). These data indicated that intestinal fibroblasts expressed DR3 and could functionally respond to direct TL1A signaling.

Example 18

Generally

Intestinal fibrostenosis is among the hallmarks of severe Crohn's disease. Patients with certain TNFSF15 (gene name for TL1A) variants over-express TL1A and have a higher risk of developing strictures in the small intestine. Additionally, sustained TL1A expression in mice leads to small and large intestinal fibrostenosis under colitogenic conditions. The inventors determined whether established murine colonic fibrosis could be reversed with TL1A antibody. Treatment with neutralizing TL1A antibody reversed colonic fibrosis back to the original pre-inflamedlevels, as result of lowered expression of connective tissue growth factor (Ctgf), IL31Ra, transforming growth factor (Tgf) β1 and insulin-like growth factor-1 (Igf1). Additionally, blocking TL1A function by either neutralizing TL1A antibody or deletion of death domain receptor 3 (DR3) reduced the number of fibroblasts and myofibroblasts, the primary cell types that mediate tissue fibrosis. Primary intestinal myofibroblasts expressed DR3 and functionally responded to direct TL1A signaling by increasing collagen and IL31Ra expression. These data demonstrated a direct role for TL1A-DR3 signaling in tissue fibrosis and that modulation of TL1A-DR3 signaling inhibits gut fibrosis.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, itis the intention of the inventors that the words and phrases in the specification and claims be given the ordinary and accustomed meanings to those of ordinary skill in the applicable art(s). The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of reversing intestinal fibrosis in a subject having inflammatory bowel disease (IBD), comprising:
   (a) assaying and detecting a high level of connective tissue growth factor (Ctgf) in a sample obtained from the subject with intestinal fibrosis, wherein the high level of Ctgf is high as compared to a level of Ctgf in a normal individual;
   (b) administering to the subject in which the high level of Ctgf was detected in (a) a therapeutically effective dosage of one or more inhibitors of tumor necrosis factor-like cytokine 1A-death domain receptor 3 (TL1A)-(DR3) binding comprising a blocking TL1A antibody; and
   (c) reducing the high level of Ctgf in the subject, thereby reversing the intestinal fibrosis in the subject, wherein reversing comprises reversal of the intestinal fibrosis to a level present in the subject prior to contracting the IBD.

2. The method of claim 1, wherein the intestinal fibrosis is colonic fibrosis.

3. The method of claim 1, wherein the Ctgf is RNA.

4. The method of claim 1, wherein reversing comprises a decrease in a number of fibroblasts and/or myofibroblasts in the subject.

5. The method of claim 1, wherein reversing comprises a decrease in a number of primary intestinal myofibroblasts in the subject.

6. The method of claim 1, wherein the IBD is Crohn's disease (CD).

7. The method of claim 6, wherein the CD is a severe form of the disease.

8. The method of claim 1, wherein the subject has strictures in a small intestine.

9. The method of claim 1, wherein the subject has intestinal fibrostenosis.

* * * * *